(12) United States Patent
Schroeder et al.

(10) Patent No.: US 9,162,432 B2
(45) Date of Patent: Oct. 20, 2015

(54) METHOD OF SEPARATING A DISCRETE PORTION FROM A WEB

(75) Inventors: Eric Louis Schroeder, Neenah, WI (US); Kirk Jon Dempsey, Appleton, WI (US); Jeffrey Alan DeBroux, Appleton, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 265 days.

(21) Appl. No.: 13/276,587

(22) Filed: Oct. 19, 2011

(65) Prior Publication Data

US 2013/0098545 A1    Apr. 25, 2013

(51) Int. Cl.
| | |
|---|---|
| A61F 13/00 | (2006.01) |
| B32B 37/16 | (2006.01) |
| B32B 38/04 | (2006.01) |
| B26D 5/00 | (2006.01) |
| B26D 7/00 | (2006.01) |
| B26F 1/44 | (2006.01) |
| B32B 37/14 | (2006.01) |
| B32B 38/00 | (2006.01) |
| A61F 13/15 | (2006.01) |
| B26F 1/38 | (2006.01) |
| B62D 5/00 | (2006.01) |
| B26D 7/08 | (2006.01) |
| B26D 7/18 | (2006.01) |

(52) U.S. Cl.
CPC ......... *B32B 37/144* (2013.01); *A61F 13/15723* (2013.01); *B26F 1/384* (2013.01); *B26F 1/3846* (2013.01); *B32B 38/0004* (2013.01); *B26D 7/086* (2013.01); *B26D 7/1863* (2013.01); *B32B 38/04* (2013.01); *B32B 2309/14* (2013.01); *B32B 2555/02* (2013.01); *B62D 5/00* (2013.01); *Y10T 83/0467* (2015.04); *Y10T 83/0577* (2015.04); *Y10T 83/0586* (2015.04); *Y10T 156/1062* (2015.01); *Y10T 156/1077* (2015.01); *Y10T 156/1085* (2015.01); *Y10T 156/1092* (2015.01)

(58) Field of Classification Search
CPC .......... B26D 5/00; B32B 38/04; B65H 37/04; B65H 39/14; B26F 1/384; Y10T 156/1084; Y10T 156/1085; Y10T 156/1092; Y10T 156/13; Y10T 156/133; Y10T 83/0448; Y10T 83/0467; Y10T 83/0577; Y10T 83/0586
USPC .............. 156/265, 302, 252, 270, 277; 83/27, 83/505, 659, 676, 23, 167, 343
See application file for complete search history.

(56) References Cited

U.S. PATENT DOCUMENTS

| | | | |
|---|---|---|---|
| 1,659,715 A * | 2/1928 | Baker et al. ..................... | 83/347 |
| 4,453,436 A | 6/1984 | Tokuno | |
| 5,235,515 A | 8/1993 | Ungpiyakul et al. | |
| 5,562,650 A | 10/1996 | Everett et al. | |
| 5,716,478 A | 2/1998 | Boothe et al. | |
| 5,826,475 A * | 10/1998 | Mysliwiec ..................... | 83/116 |
| 5,897,542 A | 4/1999 | Lash et al. | |

(Continued)

FOREIGN PATENT DOCUMENTS

| | | |
|---|---|---|
| JP | 12-16793 A | 8/1989 |
| JP | 053 17357 A | 12/1993 |

(Continued)

*Primary Examiner* — Linda L Gray

(74) *Attorney, Agent, or Firm* — Kimberly-Clark Worldwide, Inc.

(57) ABSTRACT

A method of separating a discrete portion from a first web. The discrete portion can be bonded to a second web which may be moving at the same or different speed. The discrete portion can be incorporated into an absorbent article.

18 Claims, 10 Drawing Sheets

(56) References Cited

U.S. PATENT DOCUMENTS

| | | | |
|---|---|---|---|
| 6,047,642 A | 4/2000 | Hunkeler | |
| 6,074,333 A | 6/2000 | Rajala et al. | |
| 6,149,755 A | 11/2000 | McNichols et al. | |
| 6,165,306 A | 12/2000 | Rajala | |
| 6,325,952 B1 * | 12/2001 | Jarrett et al. | 264/37.3 |
| 6,524,423 B1 | 2/2003 | Hilt et al. | |
| 6,550,517 B1 * | 4/2003 | Hilt et al. | 156/557 |
| 6,558,499 B1 | 5/2003 | Pargass et al. | |
| 6,702,917 B1 * | 3/2004 | Venturino et al. | 156/252 |
| 6,733,483 B2 | 5/2004 | Raufman et al. | |
| 6,783,622 B1 | 8/2004 | Backlund et al. | |
| 6,788,803 B2 | 9/2004 | Calvert | |
| 6,851,192 B2 * | 2/2005 | So | 30/306 |
| 6,869,386 B2 | 3/2005 | Lamping et al. | |
| 6,957,160 B2 | 10/2005 | Miller et al. | |
| 7,258,758 B2 | 8/2007 | Collier et al. | |
| 7,270,651 B2 * | 9/2007 | Adams et al. | 604/385.01 |
| 7,662,136 B2 | 2/2010 | Underhill et al. | |
| 2001/0023740 A1 | 9/2001 | Frendle et al. | |
| 2002/0062117 A1 | 5/2002 | Raufman et al. | |
| 2003/0120231 A1 * | 6/2003 | Wang et al. | 604/368 |
| 2003/0130632 A1 | 7/2003 | Costea et al. | |
| 2003/0234069 A1 | 12/2003 | Coenen et al. | |
| 2004/0143231 A1 | 7/2004 | Nair et al. | |
| 2005/0065492 A1 | 3/2005 | Cole et al. | |
| 2005/0067083 A1 | 3/2005 | Vergona | |
| 2005/0067105 A1 * | 3/2005 | Beaudry | 156/353 |
| 2006/0069372 A1 | 3/2006 | Chakravarty et al. | |
| 2006/0247594 A1 | 11/2006 | Nickel et al. | |
| 2007/0044608 A1 | 3/2007 | Franke | |
| 2008/0234643 A1 | 9/2008 | Kaneda | |
| 2010/0057035 A1 | 3/2010 | Putzer et al. | |
| 2011/0094661 A1 | 4/2011 | Thorson | |
| 2011/0135464 A1 * | 6/2011 | Luo et al. | 415/230 |

FOREIGN PATENT DOCUMENTS

| | | |
|---|---|---|
| JP | 2003-285890 A | 10/2003 |
| WO | WO 00/38606 A1 | 7/2000 |
| WO | WO 01/17473 A1 | 3/2001 |
| WO | WO 03/051228 A2 | 6/2003 |
| WO | WO 2004/004620 A1 | 1/2004 |
| WO | WO 2010/042470 A1 | 4/2010 |
| WO | WO 2010/101281 A1 | 9/2010 |

\* cited by examiner

METHOD OF SEPARATING A DISCRETE PORTION FROM A WEB

BACKGROUND

In today's consumer market, there are numerous types of products which require a discrete portion of a first web to be separated from the first web and to be bonded to a second web. Disposable absorbent articles, such as diapers, training pants, sanitary napkins, pantiliners, and incontinence products, including undergarments, briefs, pants and pads, are representative products which rely on the merging of discrete portions of a first web with a second continuous web. Many times, the first and second webs are traveling at different speeds and the transfer may need to take place at high speeds. For example, it may be necessary to bond a discrete portion of a first web to a second web at speeds exceeding 100 feet per minute.

During manufacture of the absorbent article, the first web is typically a continuous roll of material that is advanced to a forming apparatus. At the forming apparatus, sections of the first web are formed into the initial shape(s) of the discrete portion(s) while other sections of the first web are trimmed away as waste. During this forming phase of the manufacturing process, the initial shapes of the discrete portion(s) remain connected to each other via a ribbon which is a section of the first web that has not been formed into the initial shape of the discrete portion(s). The ribbon is then utilized to advance the string of discrete portions through the manufacturing process. Generally, the ribbon pulls the string of discrete portions to a converting mechanism which is typically a linear knife cutter capable of severing the discrete portion from the ribbon. The cutting is usually performed as the ribbon is advanced through a nip formed by the rotating knife coming into close proximity or contact with an anvil or backup roll. Once separated from the ribbon, the discrete portion is then carried via various rolls, typically vacuum rolls, to a location where the discrete portion can be bonded to the second web.

The use of a ribbon to transport the discrete portion, however, limits the shape, dimension and configuration of the discrete portion. As the separation of the individual discrete portion from the string of discrete portions occurs with the use of a linear knife cutter, the discrete portion has a linear cut edge in the cross-direction as it is cut. Attempting to decrease the amount of ribbon to minimize the size of the linear edge of the discrete portion can increase the amount of stress on the ribbon as it pulls the string of discrete portions through the manufacturing process. The increase in stress can result in an increase of manufacturing problems such as premature separation of the discrete portion from the first web, as well as damage, stretching, skewing, wrinkling, etc. to the discrete portion.

The use of a ribbon to transport the discrete portion further limits the shape, dimension, and configuration of the discrete portion as skewing may occur as the ribbon is pulled through the manufacturing process. The skewing of the ribbon can result in misalignment of the discrete portion at the converting mechanism. Such misalignment can result in a cutting of the discrete portion in an incorrect location at the converting mechanism. A misaligned discrete portion, therefore, can result in a malformed absorbent article which is not usable.

As a result of the shortcomings noted above, discrete portions have remained simple and uncomplicated in their shape, dimension, and configuration. Thus, there is a need for a method of manufacturing absorbent articles without the requirement of a ribbon. There is a need for a method of manufacturing absorbent articles wherein the absorbent articles can be provided with discrete portions having different shapes, dimensions and/or configurations. There is a need for proving an absorbent article having such a discrete portion.

SUMMARY

A method of forming and separating a discrete portion of a first web from the first web can have the steps of providing a first web, advancing the first web to a converting mechanism wherein the converting mechanism can be a rotary cutter with at least one die cutter shape secured thereto, cutting the first web with the die cutter shape to form a first discrete portion having a first shape without a linear cut edge in the cross-direction, and separating the first discrete portion from the first web. In an embodiment, the steps of cutting the first web and separating the first discrete portion from the first web can occur at the same time. In an embodiment, the method can further have a step of removing the first web which is no longer attached to the first discrete portion. In an embodiment, the rotary cutter can have a first die cutter shape and a second die cutter shape secured thereto which can be different. In such an embodiment, the method can further comprise the step of cutting the first web with the second die cutter shape secured to the rotary cutter to form a second discrete portion having a second shape that is different from the first shape of the first discrete portion. In an embodiment, the discrete portion can be a functional component of an absorbent article, a visual aesthetic component of an absorbent article, and combinations thereof. In an embodiment, the discrete portion can have a design graphic.

A method of bonding a discrete portion of a first web onto a second web can have the steps of providing a first web and advancing the first web at a first speed, providing a second web and advancing the second web at a second speed which is greater than the first speed, advancing the first web to a converting mechanism and forming a first discrete portion having a first shape without a linear cut edge in the cross-direction, transferring the first discrete portion from the converting mechanism onto an applicator, varying the rotational speed of the applicator to match the second speed, and transferring the first discrete portion of the first web from the applicator to the second web. In an embodiment, either the first web or the second web has at least two layers. In an embodiment, the first discrete portion has a design graphic. In an embodiment, the converting mechanism is a rotary cutter having at least one die cutter shape secured thereto. In an embodiment, the rotary cutter has at least two die cutter shapes secured to the rotary cutter and the two die cutter shapes may be different.

A method of bonding at least two discrete portions of a first web onto a second web can have the steps of providing a first web and advancing the first web at a first speed, providing a second web and advancing the second web at a second speed which is not the same as the first speed, advancing the first web to a converting mechanism and forming a first discrete portion having a first shape, transferring the first discrete portion having the first shape from the converting mechanism onto an applicator, varying the rotational speed of the applicator to match the second speed, transferring the first discrete portion having the first shape from the applicator to the second web, advancing the first web to the converting mechanism and forming a second discrete portion having a second shape, transferring the second discrete portion having the second shape from the converting mechanism onto the applicator, varying the speed of the applicator to match the second speed, and transferring the second discrete portion having the second shape from the applicator to the second web. In an embodiment, the first speed is slower than the second speed. In an embodiment, either the first web or the second web has at least two layers. In an embodiment, the converting mechanism is a rotary cutter having at least one die cutter shape secured thereto. In an embodiment, the rotary cutter has a first die cutter shape and a second die cutter shape which is different from the first die cutter shape.

DETAILED DESCRIPTION

Figure 1:
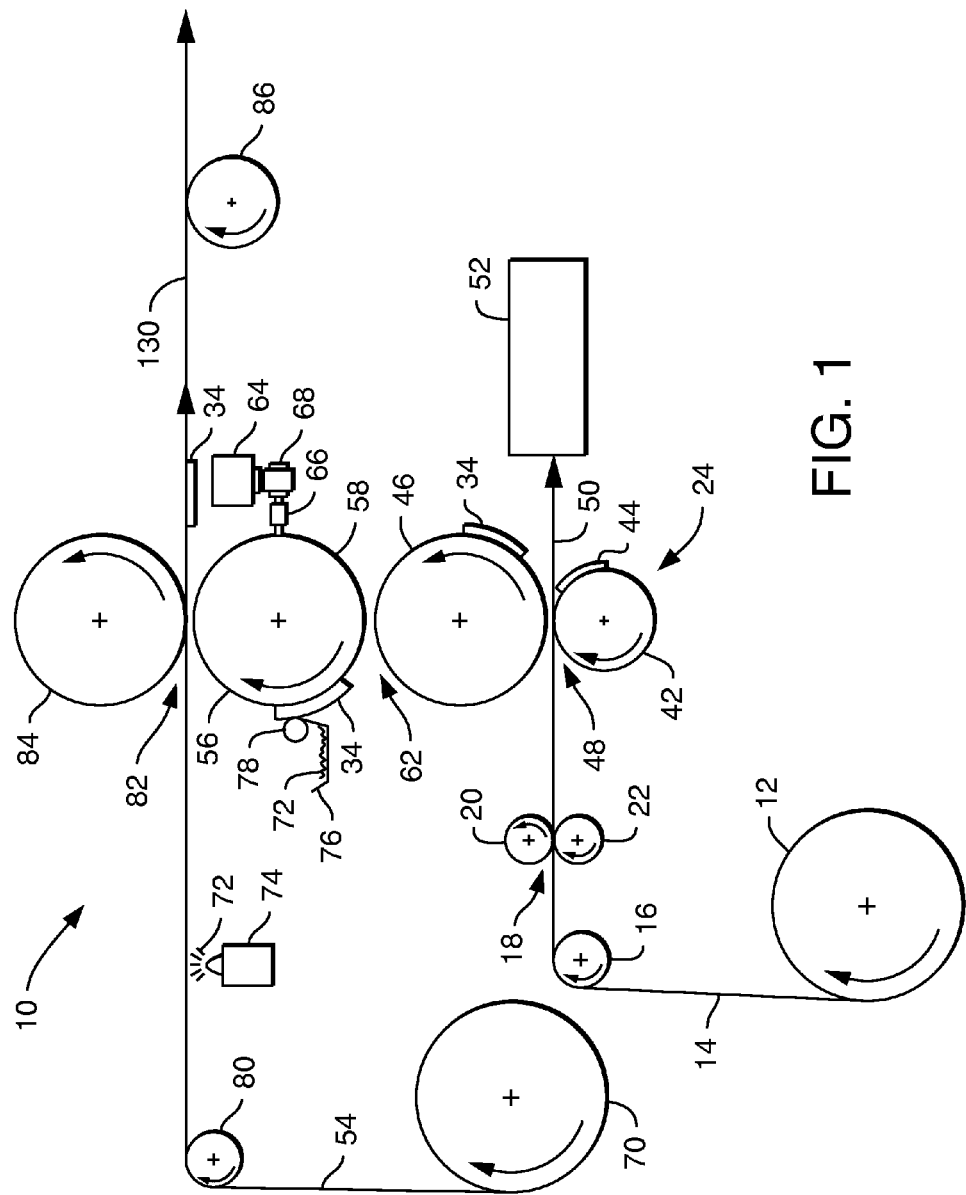
FIG. 1 is a schematic diagram of a method of transferring a discrete portion of a first web onto a second web.

The present disclosure is generally directed towards a method of separating a discrete portion from a first web. The discrete portion can be bonded onto a second web. As a non-limiting example, the method may include advancing a first web at a first speed and a second web at a second speed which may be the same as or different from the first speed. In this non-limiting example, the first web may be advanced to a converting mechanism wherein a discrete portion can be formed and separated from the first web. The discrete portion can be further advanced and can be bonded to the second web. The present disclosure is also generally directed towards an absorbent article having a discrete portion. The discrete portion can have any shape as desired. The absorbent article can have a second discrete portion which can also have any shape as desired. The shape of the second discrete portion can be the same as or different from the shape of the first discrete portion.

Definitions

The term "absorbent article" refers herein to an article which may be placed against or in proximity to the body (i.e., contiguous to the body) of the wearer to absorb and contain various liquid and solid wastes discharged from the body. Such absorbent articles, as described herein, are intended to be discarded after a limited period of use instead of being laundered or otherwise restored for reuse. It is to be understood that the present disclosure is applicable to various disposable absorbent articles including, but not limited to, diapers, training pants, youth pants, swim pants, feminine hygiene products, incontinence products, medical garments, surgical pads and bandages, other personal care or health care garments, and the like, without departing from the scope of the present disclosure.

The terms "bonded" and "bonding" refers herein to the joining, adhering, connecting, attaching, or the like, of two elements. Two elements will be considered bonded together when they are bonded directly to one another or indirectly to one another, such as when each is directly bonded to intermediate elements.

The term "film" refers herein to a thermoplastic film made using an extrusion and/or foaming process, such as a cast film or blown film extrusion process. The term includes aperture films, slit films, and other porous films which constitute liquid transfer films, as well as films which do not transfer liquid.

The term "g/cc" refers herein to grams per cubic centimeter.

The term "gsm" refers herein to grams per square meter.

The term "hydrophilic" refers herein to fibers or the surfaces of fibers which are wetted by aqueous liquids in contact with the fibers. The degree of wetting of the materials can, in turn, be described in terms of the contact angles and the surface tensions of the liquids and materials involved. Equipment and techniques suitable for measuring the wettability of particular fiber materials or blends of fiber materials can be provided by a Cahn SFA-222 Surface Force Analyzer System, or a substantially equivalent system. When measured with this system, fibers having contact angles less than 90 are designated "wettable" or hydrophilic, and fibers having contact angles greater than 90 are designated "nonwettable" or hydrophobic.

The term "liquid impermeable" refers herein to a layer or multi-layer laminate in which the liquid body waste, such as urine, will not pass through the layer or laminate, under ordinary use conditions, in a direction generally perpendicular to the plane of the layer or laminate at the point of liquid contact.

The term "liquid permeable" refers herein to any material that is not liquid impermeable.

The term "meltblown" refers herein to fibers formed by extruding a molten thermoplastic material through a plurality of fine, usually circular, die capillaries as molten threads or filaments into converging high velocity heated gas (e.g., air) streams which attenuate the filaments of molten thermoplastic material to reduce their diameter. Thereafter, the meltblown fibers are carried by the high velocity gas stream and are deposited on a collecting surface to form a web of randomly dispersed meltblown fibers. Such a process is disclosed, for example, in U.S. Pat. No. 3,849,241 to Butin et al. which is incorporated herein by reference. Meltblown fibers are microfibers which may be continuous or discontinuous, are generally smaller than about 0.6 denier, and are generally self-bonding when deposited onto a collecting surface. Meltblown fibers used in the present disclosure may be continuous in length.

The term "non-woven" refers herein to materials and webs of material which are formed without the aid of a textile weaving or knitting process.

The term "pliable" refers herein to materials which are compliant and which will readily conform to the general shape and contours of the wearer's body.

The term "spunbond" refers herein to small diameter fibers which are formed by extruding molten thermoplastic material as filaments from a plurality of fine capillaries of a spinnerette having a circular or other configuration, with the diameter of the extruded filaments then being rapidly reduced by a conventional process such as that described in U.S. Pat. No. 4,340,563 to Appel et al., U.S. Pat. No. 3,692,618 to Dorschner et al., U.S. Pat. No. 3,802,817 to Matsuki et al., U.S. Pat. Nos. 3,338,992 and 3,341,394 to Kinney, U.S. Pat. No. 3,502,763 to Hartmann, U.S. Pat. No. 3,502,538 to Peterson, and U.S. Pat. No. 3,542,615 to Dobo et al., each of which is incorporated herein in its entirety by reference. Spunbond fibers are generally continuous and often have average deniers larger than about 0.3, and in an embodiment, between about 0.6 and about 10.

The term "superabsorbent" refers herein to a water-swellable, water-insoluble organic or inorganic material capable, under the most favorable conditions, of absorbing at least about 15 times its weight and, in an embodiment, at least about 30 times its weight, in an aqueous solution containing 0.9 weight percent sodium chloride. The superabsorbent materials can be natural, synthetic and modified natural polymers and materials. In addition, the superabsorbent materials can be inorganic materials, such as silica gels, or organic compounds, such as cross-linked polymers.

The term "surge layer" refers herein to a layer capable of rapidly accepting and temporarily holding liquid body waste to decelerate and diffuse a surge or gush of liquid body waste and to subsequently slowly release the liquid body waste therefrom into another layer or layers of the absorbent article.

The term "thermoplastic" refers herein to a material which softens when exposed to heat and which substantially returns to a non-softened condition when cooled to room temperature.

Referring to FIG. 1, a schematic is depicted for a method of forming a discrete portion of a first web, separating the discrete portion from the first web and bonding the discrete portion onto a second web when the first and second webs are traveling at the same or different speeds. The method uses an apparatus 10 that includes a supply roll 12 having a first web 14. The first web 14 can be any kind of material as desired. Typical materials include, but are not limited to, paper, cellulose fibers, pulp, plastic film, cloth, non-woven materials including, but not limited to, spunbond, and various synthetic and non-synthetic materials. The first web 14 can be a composite formed from two or more similar or different materials joined together. The first web 14 can be a laminate formed from two or more layers of material. The first web 14 can be primed or treated with a coating. The first web 14 can be flexed or otherwise manipulated to provide certain desirable properties. An adhesive can be applied to at least one side of the first web 14, if desired. The adhesive, however, should not have such a strong peel strength that it would stick to downstream manufacturing equipment. The first web 14 can be a continuous thin sheet or strip or it can have a three dimensional profile. For example, the first web 14 can be flat, lofty or bulky and may vary in thickness in the longitudinal and/or transverse directions.

The first web 14 can have any width that can be accommodated by the manufacturing equipment it is designed to run on. In an embodiment, the width of the first web 14 may be equal to or less than about 24, 20, 18, 15, 10, 7, 6, 5, 4, 3, 2 or 1 inches. The length of the first web 14, measured parallel to the machine direction, is generally greater than the width of the first web 14. The length of the first web 14 may be as long as practicably feasible so as to decrease the number of changeovers required. The first web 14 is generally considered "continuous" if it has only one beginning and one ending point on the supply roll 12.

The first web 14 may be advanced from the supply roll 12 around one or more guide rolls 16 (only one of which is depicted). The number of guide rolls 16 can vary depending on a number of factors, including the length and width of the first web 14, the distance the first web 14 has to travel, the desired tension, etc. The first web 14 can be advanced through a nip 18 formed by the contact between a pair of feed rolls 20 and 22. One or both of the feed rolls 20 and 22 can be driven, that is, rotated by a motor, to advance the first web 14. More than one pair of feed rolls 20 and 22 can be used if one wishes to stretch the first web 14. In an embodiment, the pair of feed rolls 20 and 22 can be driven so as to pull or draw the first web 14 away from the supply roll 12 and toward a converting mechanism 24.

The converting mechanism 24 may be capable of forming the discrete portion 34 and separating the discrete portion 34 from the first web 14. As noted above, the initial shape of the discrete portion has typically been formed from the first web prior to the ribbon of formed discrete portions advancing to the converting mechanism where the discrete portion was separated from the ribbon by the converting mechanism. As noted above, the typical manufacturing process resulted in a discrete portion having a linear cut edge on a side of the discrete portion as it is cut in a cross-direction by a linear knife thereby limiting the shape of the discrete portion. According to the current disclosure, the forming of the discrete portion 34 and the separating of the discrete portion 34 from the first web 14 can both occur at the converting mechanism 24. In an embodiment, a discrete portion 34 may be formed without having a connection, or a ribbon, to another discrete portion 34. In an embodiment, a discrete portion 34 may be formed without a cross-directional linear cut edge. In an embodiment, a discrete portion 34 having curved edges on all side edges may be formed. In an embodiment, a discrete portion 34 having any desired shape, dimension, and/or configuration may be formed. In an embodiment, a discrete portion 34 having unique and/or complicated shapes may be formed. In an embodiment, multiple discrete portions 34 having different shapes from each other may be formed from the same first web 14.

The converting mechanism 24 can be any type of device needed to cut, slice, die cut, stamp, or form a discrete portion 34 of desired shape, dimension, and/or configuration from the first web 14. For example, in an embodiment, the converting mechanism 24 can be a rotary cutter 42 and may have one or more die cutter shapes 44 secured about the outer periphery of the rotary cutter 42. Other suitable cutting apparatuses could be used such as, for example, knives, a die, a stamp, an ultrasonic device, or any other suitable device known to those skilled in the art. One die cutter shape 44 is shown secured to the rotary cutter 42 in FIG. 1 and it is to be understood that additional die cutter shapes 44 may be secured thereto. The die cutter shape(s) 44 can be configured on the rotary cutter 42 to form the first web 14 into a discrete portion 34 having any desired shape, such as a rectangle, square, circle, oval, hourglass or any other desired shape. The discrete portion 34 can be any size or shape as desired. The discrete portion 34 may have a width as wide as the width of the first web 14 or may have a width smaller than the total width of the first web 14. The discrete portion 34 may have a shape ranging from simple to complex. The discrete portion 34 may be symmetrical or asymmetrical. The discrete portion 34 may have a shape 32 that is uniform or non-uniform.

In an embodiment in which the converting mechanism 24 is a rotary cutter 42, the rotary cutter 42 can cooperate with and can be positioned in close proximity to an anvil roll 46 and form a gap 48 therebetween. The rotary cutter 42 will rotate and bring the die cutter shape 44 into contact with or be aligned to be very close to the outer surface of the anvil roll 46 and will form a nip with the anvil roll 46 as the first web 14 is advanced to the converting mechanism 24 such that the discrete portion 34 can be formed and separated from the first web 14. The rotary cutter 42 may have any diameter as desired. It should be understood that the greater the diameter of the rotary cutter 42, the greater the number of die cutter shapes 44 that can be secured to the rotary cutter 42. An increase in the number of die cutter shapes 44 that are secured to the rotary cutter 42 can result in an increase in the number of discrete portions 34 formed and separated from the first web 14 in a rotation, an increase in the variety of the formed and separated discrete portions 34, and combinations thereof.

A rotary cutter 42 may have at least one die cutter shape 44 secure thereto. A rotary cutter may have 2, 3, 4, 5 or 6 die cutter shapes 44 secured thereto. In an embodiment in which the rotary cutter 42 has at least two die cutter shapes 44 secured thereto, the at least two die cutter shapes 44 may be configured to form discrete portions 34 having the same shape 32. In another embodiment in which the rotary cutter 42 has at least two die cutter shapes 44 secured thereto, the at least two die cutter shapes 44 may be configured to form discrete portions 34 having different shapes 32. In an embodiment in which the rotary cutter 42 has at least two die cutter shapes 44 secured thereto, the die cutter shapes 44 may be secured to the rotary cutter 42 in a sequence that will correspond to a desired sequence of shapes of discrete portions 34 to be formed as the first web 14 is advanced to the converting mechanism 24. As the rotary cutter 42 rotates, a die cutter shape 44, corresponding to a desired shape of a discrete portion 34 to be formed from the first web 14, will cut the first web 14 thereby forming the discrete portion 34 which will have a shape corresponding to the die cutter shape 44. As the rotary cutter 42 continues to rotate, the second die cutter shape 44 secured to the rotary cutter 42 will cut the first web 14 thereby forming the next sequential discrete portion 34 which will have a shape corresponding to the second die cutter shape 44. As noted above, the sequence of the die cutter shapes 44 on the rotary cutter 42 can vary and, therefore, the corresponding sequence of shapes of formed discrete portions 34 can vary. It should be noted that the multiple die cutter shapes 44 secured to a rotary cutter 42 may be configured to be in-phase or out-of-phase with regards to each other. In an embodiment, a rotary cutter 42 with at least two die cutter shapes 44 secured thereto in an in-phase configuration can form and separate from the first web 14 at least two discrete portions 34 that are parallel to each other. In an embodiment, a rotary cutter 42 with at least two die cutter shapes 44 secured thereto in an out-of-phase configuration can form and separate from the first web 14 at least two discrete portions 34 from different areas of the first web 14 which may not be parallel to each other.

In FIG. 1, the rotary cutter 42 is illustrated as rotating in a clockwise direction while the anvil roll 46 is rotated in a counterclockwise direction. It should be understood that the rotation of the equipment can be arranged as deemed suitable by one of ordinary skill. In an embodiment, both the rotary cutter 42 and the anvil roll 46 can have the same outside diameter and can rotate at the same speed. However, the rotary cutter 42 and the anvil roll 46 do not need to have the same outside diameter and can be set-up to rotate at the same or at different speeds.

In the illustrated schematic of FIG. 1, as the first web 14 passes through the gap 48 and is contacted by the die cutter shape 44, a discrete portion 34 will be formed for each 360-degrees of rotation of the rotary cutter 42. It should be noted that when the rotary cutter 42 has more than one die cutter shape 44 secured to its outer surface, a discrete portion 34 will be formed for each partial rotation of the rotary cutter 42. In an embodiment, the shape of the discrete portion 34 can be such that trim waste 50 may be present after the discrete portion 34 is formed and separated from the first web 14. This trim waste 50 can be directed to a recycling hopper 52 where it can be collected and later reused to make new material. The trim waste 50 can be in the form of a single continuous strip or it can consist of a plurality of smaller individual pieces.

It should be understood that a plurality of discrete portions 34 may be formed and separated in parallel from the first web 14 and transferred to the second web 54. In an embodiment in which parallel discrete portions 34 are formed and separated from the first web 14, the parallel discrete portions 34 may be advanced through the remainder of the manufacturing process sequentially or in parallel. As described herein, the parallel discrete portions 34 may have the same or different shape and/or the same or different graphic. It should be understood that the method described herein can apply to discrete portions 34 being formed and separated from multiple first webs 14. In other words, multiple first webs 14 may be advanced to either the same or different converting machines 24 and multiple discrete portions 34 can be formed and separated from each of the multiple first webs 14.

The discrete portion 34 may be a functional component of the absorbent article, may be a visual aesthetic component of the absorbent article, and combinations thereof. Examples of functional components include, but are not limited to, absorbent cores, surge layers, fasteners, waistband elements, etc. Examples of visual aesthetic components include, but are not limited to, graphics for various components of the absorbent article such as, but not limited to, the outer cover, the bodyside liner, fasteners, waistband elements, etc. It should be understood that the shape of the discrete portion 34 may also be a visual aesthetic component. It should be understood that the discrete portion 34 may be a combination of a functional component and a visual aesthetic component. As will be described herein, multiple discrete portions 34 can be formed and separated from the first web 14. As described herein, in an embodiment, each discrete portion 34 can be the same as another discrete portion 34 formed and separated from the same first web 14. Also as described herein, a discrete portion 34 can be different from another discrete portion 34 formed and separated from the same first web 14.

In an embodiment, it may be desired that the discrete portion 34 be a functional component and the first web 14 may be constructed in any manner as necessary to create the desired characteristics of the functional component. For example, in an embodiment, it may be desired that the discrete portion 34 be an absorbent core for an absorbent article. The first web 14, therefore, may have the desired absorbent core materials present in the desired combination of materials and in the desired thickness. It may also be desired that the absorbent core have an hourglass shape. The first web 14 can advance to the converting mechanism 24 having, for example, a rotary cutter 42 with an hourglass shape die cutter shape 44 secured thereto. The rotary cutter 42 can be configured to operate at the same speed at which the first web 14 is moving and the die cutter shape 44 can cut the first web 14 to form the discrete portion 34 which can be the absorbent core having an hourglass shape. As the discrete portion 34 is formed, it can be separated from the first web 14. The remainder of the first web 14 not formed into the discrete portion 34 can be removed as trim waste which can be reclaimed. It should be understood that each absorbent core formed and separated from the first web 14 may be the same as all other absorbent cores formed and separated from the same first web 14. It should be understood that each absorbent core formed and separated from the first web 14 may be different from at least one other absorbent core formed and separated from the same first web 14. Examples of differences include, but are not limited to, shape (e.g., hourglass, rectangle, etc.), thickness, materials used to create the first web 14, size dimensions (e.g. length, width, etc.), etc. It should be understood that the first web 14 may, but need not, have a graphic associated therewith. A graphic, if present, may be a part of the discrete portion 34.

In an embodiment, it may be desired that the discrete portion 34 be a fastener for an absorbent article. The first web 14, therefore, may be configured to have any characteristics as desired, such as, for example, hook or loop material, elastomeric material, and combinations thereof. The first web 14 can be advanced to the converting mechanism 24, such as a rotary cutter 42 with a die cutter shape 44 secured thereto. The die cutter shape 42 can be configured to form a discrete portion 34 from the first web 14 into any shape as desired and separate the discrete portion 34 from the first web 14. The remainder of the first web 14 not formed into the discrete portion 34 can be removed as trim waste which can be reclaimed. It should be understood that each fastener formed and separated from the first web 14 may be the same as all other fasteners formed and separated from the first web 14. It should be understood that each fastener formed and separated from the same first web 14 may be different from at least one other fastener formed and separated from the same first web 14. Examples of differences include, but are not limited to, shape, size dimensions, etc. It should be understood that the first web 14 may, but need not, have a graphic associated therewith. A graphic, if present, may be a part of the discrete portion 34.

In an embodiment in which it may be desired that the discrete portion 34 be a visual aesthetic component, the first web 14 may be advanced to the converting mechanism 24 with or without a design graphic 26 associated therewith. FIGS. 2-6 provide example illustrations of design graphics 26. The design graphic 26 may illustrate a graphic 28 desired to be incorporated into the absorbent article 200. The graphic 28 can have any colors and/or imagery as desired. The perimeter 30 of the design graphic 26 may provide an illustration of the shape 32 of the discrete portion 34. The association of a design graphic 26 with the first web 14 may occur through any means deemed suitable such as, for example, printing. The design graphic 26 may be associated with the first web 14 prior to the first web 14 being placed onto the first supply roll 12, after the first web 14 advances off of the first supply roll 12, or prior to the first web 14 advancing to the converting mechanism 24. It should be understood that the design graphic 26 may be associated with the discrete portion 34 after the discrete portion 34 has been formed and separated from the first web 14. The design graphic 26 associated with the first web 14 may be present on the first web 14 in as many repetitions as desired. As a non-limiting example, if one desired to form 100 discrete portions 34 having the same design graphic 26, 100 repetitions of the same design graphic 26 would be associated with the first web 14. The first web 14 may have one design graphic 26 associated therewith or the first web 14 may have more than one design graphic 26 associated therewith. In an embodiment in which multiple design graphics 26 are associated with the first web 14, the multiple design graphics 26 may be repetitions of a same design graphic 26, may be different design graphics 26, or combinations thereof (for example, a first design graphic may be the same as a second design graphic and different from a third design graphic.).

The perimeter of the design graphic 26 may illustrate a shape 32 that resembles the shape of the graphic 28 illustrated in the design graphic 26. For example, the graphic 28 may be an illustration of a hand or paw and the contours of the perimeter 30 of the design graphic 26 may resemble the contours of the hand or paw, respectively. In an embodiment, the graphic 28 may extend to the perimeter 30 of the design graphic 26 and, therefore, the outer edge of the graphic 28 may be contiguous with the perimeter 30 of the design graphic 26. In such an embodiment, the discrete portion 34 having such a design graphic 26 may have a graphic 26 contiguous with the edges of the discrete portion 34. In an embodiment, the graphic 28 does not necessarily extend to the perimeter 30 of the design graphic 26. In such an embodiment, the graphic 28 may be smaller than the discrete portion 34 having such a design graphic 26. In an embodiment, the graphic 28 and/or design graphic 26 may be larger than the discrete portion 34 to be formed. In an embodiment, a first web 14 having more than one design graphic 26 associated therewith, prior to the forming of the discrete portion 34, may have a perimeter 30 of each design graphic 26 providing an illustration of more than one shape 32 of discrete portions 34 to be formed. In an embodiment, each design graphic 26 may have a perimeter 30 illustrating the same shape 32. For example, a first web 14 having at least two design graphics 26 may have perimeters 30 providing illustrations of the same shape 32. As another example, a first web 14 having at least two design graphics 26 may have perimeters 30 of each design graphic 26 providing illustrations of different shapes 32 of the discrete portions 34 to be formed and separated from the first web 14.

In an embodiment, the first web 14 may have at least two design graphics 26 associated therewith and the at least two design graphics 26 may illustrate the same graphic 28 or different graphics 28. In an embodiment, a first web 14 may have at least two design graphics 26 associated therewith and each design graphic 26 may illustrate the same graphic 28. In such an embodiment, the perimeters 30 of the at least two design graphics 26 may illustrate the same shape 32 or may illustrate different shapes 32. In an embodiment, a first web 14 may have at least two design graphics 26 printed thereon and each design graphic 26 may illustrate a different graphic 28. In such an example, the different graphics 28 may be, but need not be, related to each other, such as, for example, by theme, color, activity, etc. It should be understood that the design graphics 26 exemplified above may have perimeters 30 illustrating the same or different shape 32 regardless of whether the design graphics 26 illustrate the same or different graphic 28.

Figure 2:
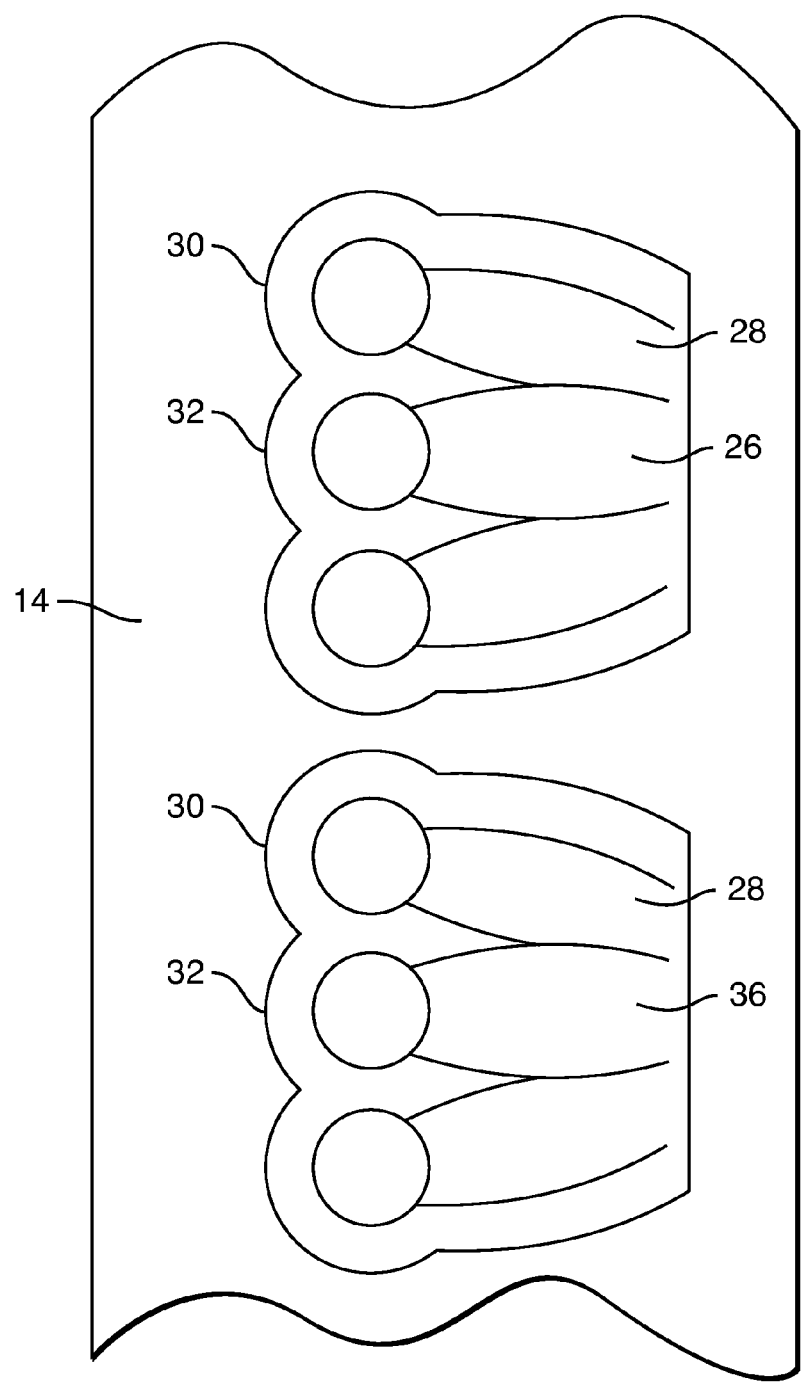
FIG. 2 is a top view of an embodiment of a first web having two design graphics associated therewith.
Figure 3:
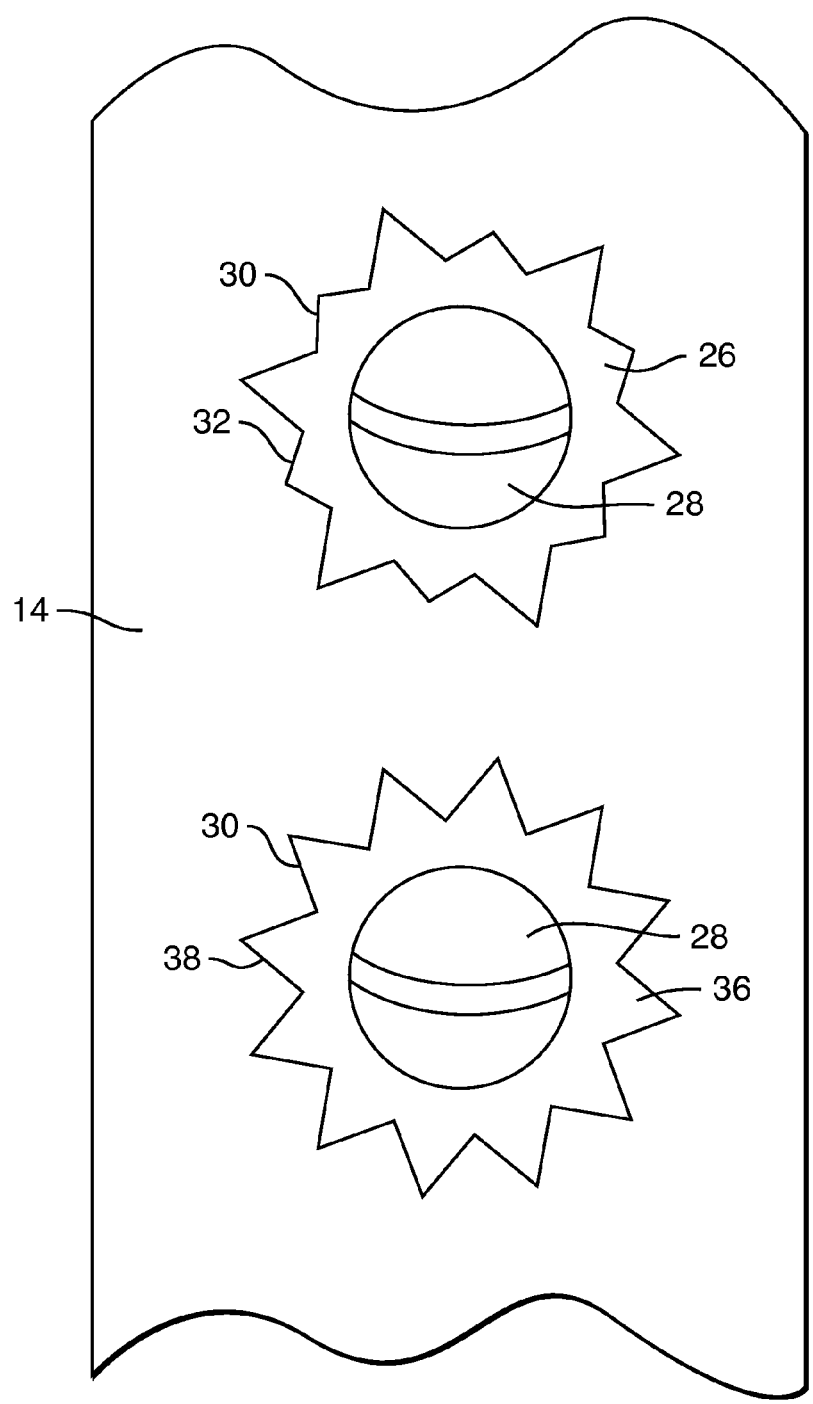
FIG. 3 is a top view of another embodiment of a first web having two design graphics associated therewith.
Figure 4:
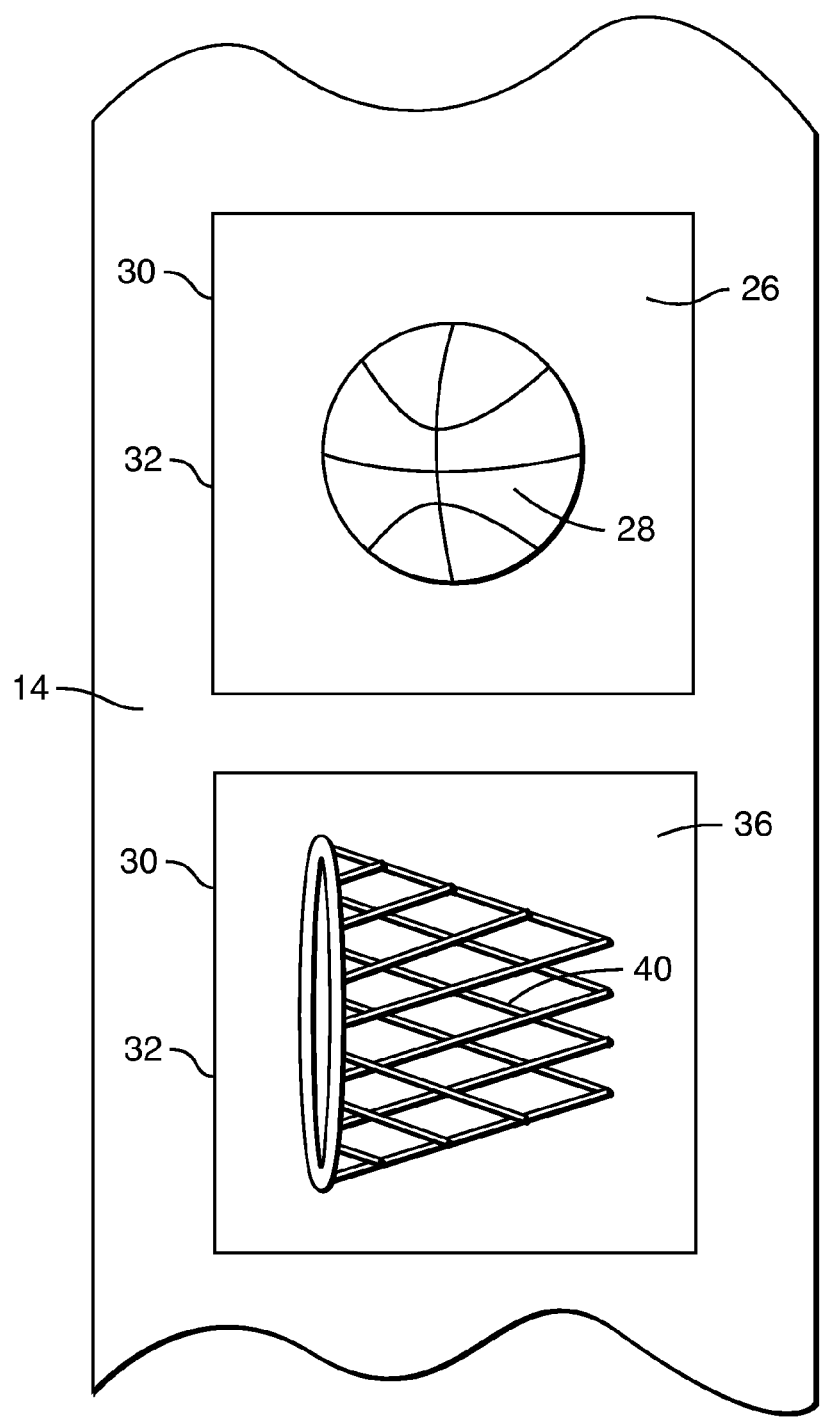
FIG. 4 is a top view of another embodiment of a first web having two design graphics associated therewith.
Figure 5:
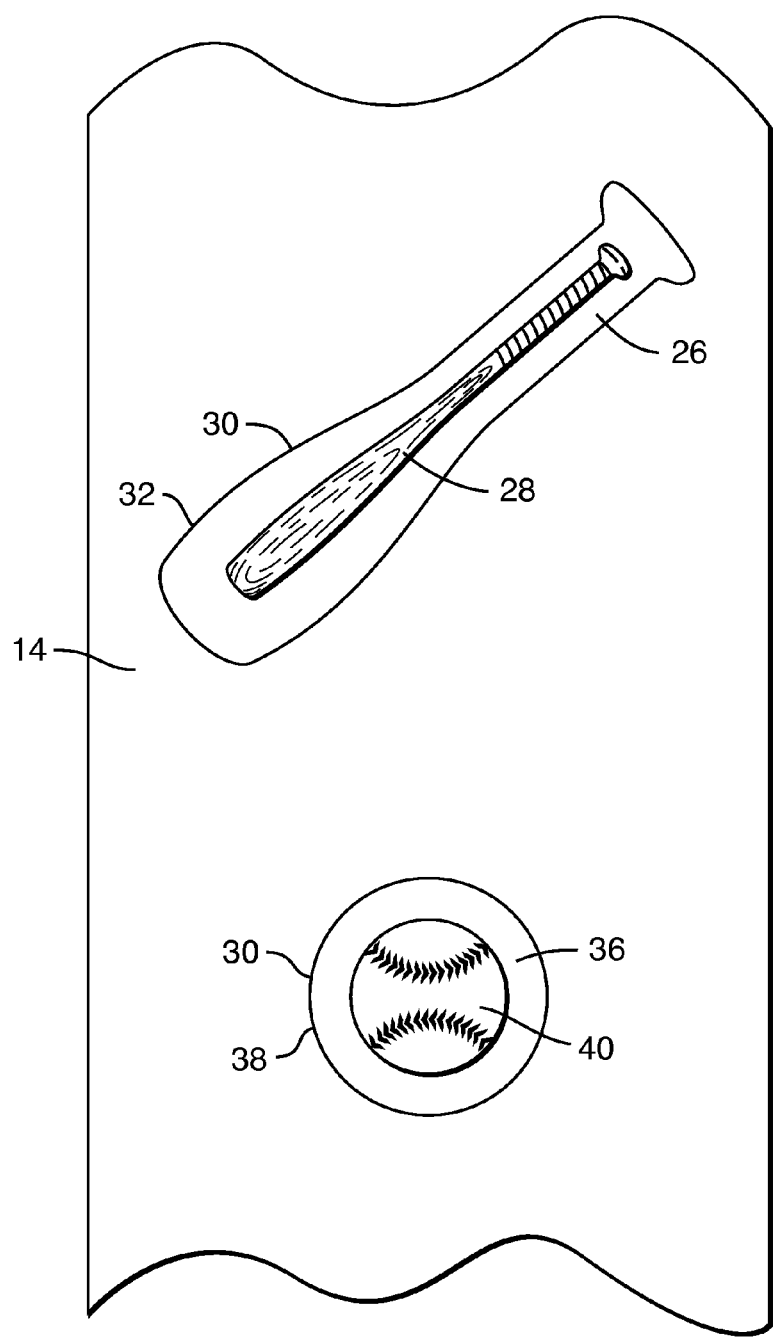
FIG. 5 is a top view of another embodiment of a first web having two design graphics associated therewith.
Figure 6:
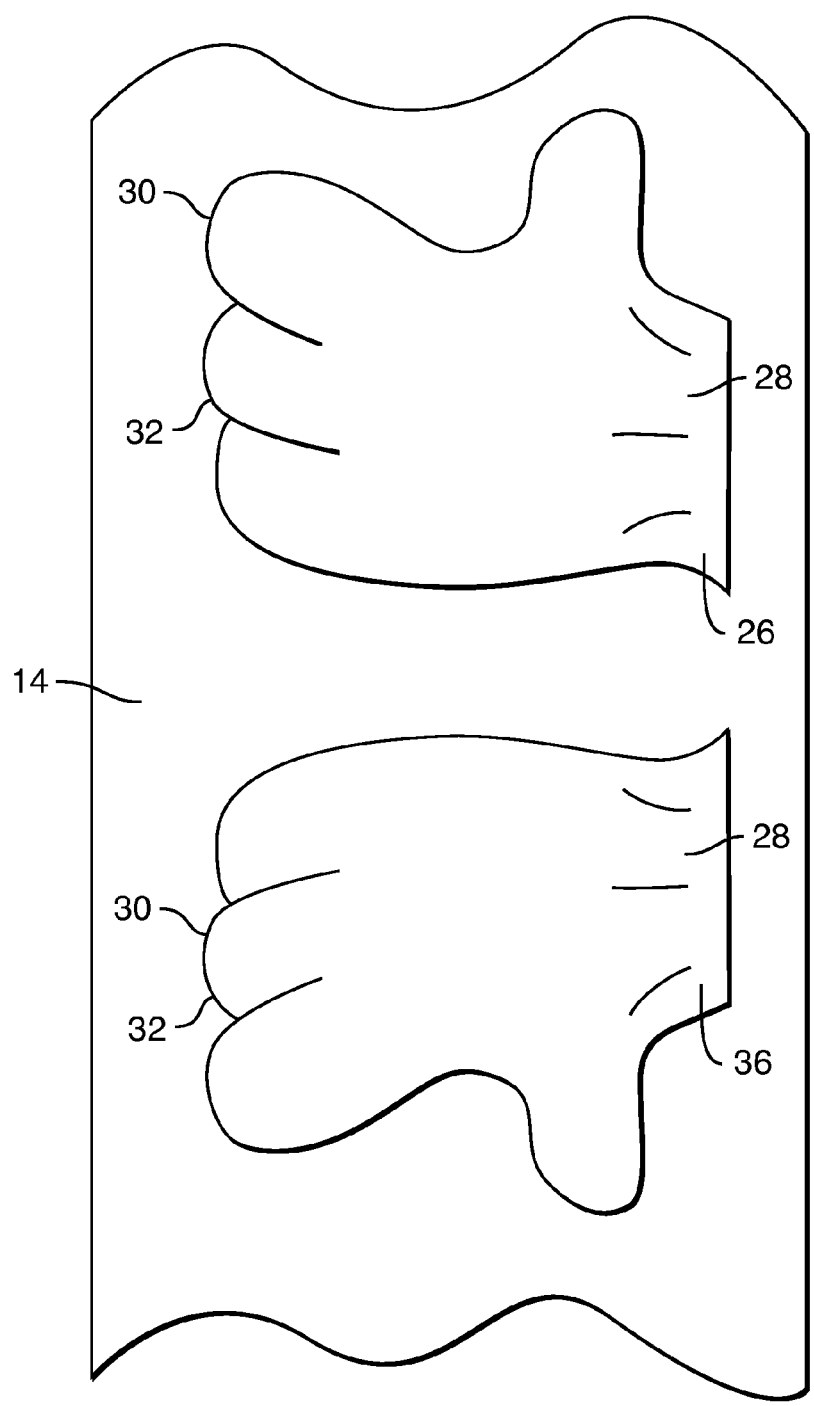
FIG. 6 is a top view of another embodiment of a first web having two design graphics associated therewith.

As noted above, therefore, and referring to FIGS. 2-5, a first web 14 having at least two design graphics 26 associated therewith may have at least two design graphics 26 associated with the first web 14 in a variety of combinations: 1) a first design graphic 26 and a second design graphic 36 may illustrate the same graphic 28 and the perimeter 30 of the design graphics, 26 and 36, may illustrate the same shape 32 (FIG. 2); 2) a first design graphic 26 and a second design graphic 36 may illustrate the same graphic 28 and the perimeter 30 of the two design graphics, 26 and 36, may illustrate first and second shapes, 32 and 38 (FIG. 3); 3) a first design graphic 26 and a second design graphic 36 may illustrate first and second graphics, 28 and 40, and the perimeter 30 of the two design graphics, 26 and 36, may illustrate the same shape 32 (FIG. 4); and 4) a first design graphic 26 and a second design graphic 36 may illustrate first and second graphics, 28 and 40, and the perimeters 30 of each of the design graphics, 26 and 36, may illustrate first and second shapes, 32 and 38, (FIG. 5). It should be understood that FIG. 2 provides an illustration of two repetitions of the same design graphic 26. FIG. 6 provides an illustrative example of two design graphics 26 associated with a first web 14 in an embodiment in which a first design graphic 26 and a second design graphic 36 illustrate mirror images, as the first web 14 is viewed in a top down view, of a graphic 28 and shape 32. It should be understood that while the combinations described above have been described with regards to only two design graphics, 26 and 36, associated with the first web 14, one of ordinary skill would be able to apply the same types of combinations and variations thereof to a first web 14 having more than two design graphics 26 associated therewith.

In an embodiment wherein the first web 14 has at least two design graphics, 26 and 36, associated therewith, the design graphics, 26 and 36, may be in any sequence as desired. In such an embodiment, the at least two design graphics, 26 and 36, may differ from each other. For example, the at least two design graphics, 26 and 36, may illustrate different graphics, shapes, and/or combinations thereof. In an embodiment, the first web 14 may have two design graphics, 26 and 36, associated therewith in an alternating sequence. The first design graphic 26 may occupy a first position on the first web 14, followed by the second design graphic 36 which can be followed by the first design graphic 26, and so on, in a repeating sequence, until the desired number of repetitions of each design graphic, 26 and 36, have been associated with the first web 14. It should be understood that this sequence and variations thereof may be applied to any number of design graphics 26 associated with the first web 14.

In an embodiment, the first web 14 has at least two design graphics, 26 and 36, associated therewith in an alternating sequence wherein two repetitions of the first design graphic 26 are followed by two repetitions of the second design graphic 36, followed by two repetitions of the first design graphic 26, and so on, in a repeating sequence, until the desired number of repetitions of each design graphic, 26 and 36, have been associated with the first web 14. It should be understood that this sequence and variations thereof can be applied to any number of design graphics 26 associated with the first web 14. In such an embodiment, the at least two design graphics, 26 and 36, may differ from each other. For example, the at least two design graphics, 26 and 36, may illustrate different graphics, shapes, and/or combinations thereof.

In FIG. 1, after the discrete portion 34 is formed by the converting mechanism 24, the discrete portion 34 can be separated from the first web 14 and transferred from the converting mechanism 24 to the outer surface of the anvil roll 46. As the anvil roll 46 is rotated, the discrete portion 34 is carried away from both the converting mechanism 24 and from the trim waste 50. A vacuum can be used to assist in holding the discrete portion 34 on the outer surface of the anvil roll 46. The vacuum or suction needed to hold the discrete portion 34 against the outer surface of the anvil roll 46 can be adjusted to meet one's needs depending on the size, shape, weight, dimensions and material characteristics of the discrete portion 34. Typically, the anvil roll 46 is constructed of a strong material, such as steel, cast iron, aluminum, hard rubber or a hard thermoplastic material. In an embodiment, the outer surface of the anvil roll 46 can be coated to make it smooth and/or slick. In an embodiment, the outer surface of the anvil roll 46 could be treated or machined to form a non-skid surface, a textured surface or a surface of high friction. It should be noted that the outside diameter of the anvil roll 46 may be any desired dimension. It should be understood that, in an embodiment, the positioning of the converting mechanism 24 and the anvil roll 46 may be reversed. In such an embodiment, the discrete portion 34 may remain on the converting mechanism 24 following the separation of the discrete portion 34 from the first web 14. In such an embodiment, the converting mechanism 24 may have the ability to transfer the discrete portion 34 to an applicator, such as described herein, or any other alternate apparatus or located as desired. For example, the discrete portion 34 may be transferred from the converting mechanism 24 to a conveyor belt (not shown) for continued movement through the manufacturing process. The discrete portion 34 may be transferred from the converting mechanism 24 to another location of the manufacturing process where it can be bonded to another discrete portion prior to be bonded to the second web 54.

In an embodiment in which the converting mechanism 24 is a rotary cutter, the rotational surface speed of the anvil roll 46 can be slower than, equal to or greater than the rotational surface speed of the rotary cutter 42. In an embodiment, the rotational speed of the rotary cutter 42 and the anvil roll 46 are the same. In an embodiment, the anvil roll 46 may rotate at a rotational speed at least equal to the speed of the first web 14 and, in another embodiment, at a faster speed. In an embodiment, depending on the length of the discrete portion 34, the discrete portion 34 can be at least partially located on the outer surface of the anvil roll 46 while the die cutter shape 44 is forming and cutting the opposite end of the discrete portion 34. In an embodiment, the discrete portion 34 will slip on the anvil roll 46 when the feed rate of the first web 14 is slower than the surface speed of the rotary cutter 42 or the anvil roll 46. To ensure a smooth slip of the discrete portion 34 on the outer surface of the anvil roll 46 with decreased binding, gapping and pulling, it may be desirable to size the gap 48 to have a minimal clearance. The discrete portion 34 can then continue to slip on the anvil roll 46 until it is completely formed and cut by the die cutter shape 44. The actual severance of the discrete portion 34 from the first web 14 will release the discrete portion 34 and allow the discrete portion 34 to be completely transferred to the anvil roll 46. It should be noted that the discrete portion 34, when completely severed from the first web 14, can adhere to the outer surface of the anvil roll 46 and, therefore, travel at the rotational speed of the anvil roll 46.

The discrete portion 34 can adhere to the outer surface of the anvil roll 46 because of the vacuum being pulled from within the anvil roll 46. Generally, the outer surface of the anvil roll 46 can have a plurality of small holes formed therein that are connected to a source of vacuum. The force of the vacuum can range from about 0.1 inches of water pressure to about 50 inches of water pressure. In an embodiment, the force of the vacuum can be less than about 30 or 15 inches of water pressure. The amount of vacuum that will be needed will also be dependent upon the porosity of the material from which the discrete portion 34 is formed. The surface area of the discrete portion 34 over which the vacuum will act may also change and should be taken into consideration when calculating the amount of vacuum needed.

The discrete portion 34 can be transferred from the anvil roll 46 onto an applicator 56. In an embodiment, the applicator 56 may be a transfer roll 58 as described hereinbelow. In another embodiment, the applicator 56 may be an oscillating cam adjusted roll 60 as described hereinbelow. The function of the applicator 56 is to transport the discrete portion 34 toward a second web 54. It should be understood that the discrete part 34 may be bonded to the second web 54 by means of an adhesive applied in a selected pattern to the surface of the discrete part 34, or by any other suitable means for bonding the discrete part 34 to the second web 54.

In an embodiment, as illustrated in FIG. 1, in which the applicator 56 is a transfer roll 58, the two rolls, anvil roll 46 and transfer roll 58, are positioned in close proximity to one another and are arranged to form a gap 62 therebetween to permit the discrete portion 34 to be transferred onto the outer surface of the transfer roll 58 without being unduly compressed. The transfer roll 58 can have a diameter that is smaller than, equal to or larger than the diameter of the anvil roll 46. In an embodiment, the transfer roll 58 can have the same diameter as the anvil roll 46. The transfer roll 58 can be a vacuum roll. The transfer roll 58 can be constructed of similar materials as the anvil roll 46. Typical materials include, but are not limited to, steel, aluminum, hard rubber or a hard thermoplastic material. Alternatively, the transfer roll 58 can be constructed from low inertia materials such as, but not limited to, composite materials, graphite, a polycarbonate material, carbon fiber, or nylon.

An adjustable, variable speed servomotor 64 may drive the transfer roll 58 via a connector 66. A variable speed servomotor 64 may enable the transfer roll 58 to accelerate and/or decelerate quickly within a single revolution. The transfer roll 58 may, therefore, increase and/or decrease its speed during each 360-degree rotation. In an embodiment, it may be desirable to transfer a discrete portion 34 of a first web 14, which is travelling at a first speed, onto a second web 54 which is travelling at a second speed. The first and second speeds may be different or they may be the same. In an embodiment, the second speed may be faster than the first speed. In an embodiment, the speed of the transfer roll 58 may be changed from a first speed to a second speed after the discrete portion 34 is transferred from the anvil roll 46 to the transfer roll 58. This may provide a smooth transfer and may reduce any shock, gapping, or pulling on the discrete portion 34. The speed of the transfer roll 58 can be controlled by "step" inputs, such as, a sudden and immediate change from a first speed to a second speed or it can be controlled by "ramp" inputs. In an embodiment, the first speed of the transfer roll 58 may correspond to the speed of the anvil roll 46 and the second speed of the transfer roll 58 may correspond to the speed of the second web 54.

Figure 7:
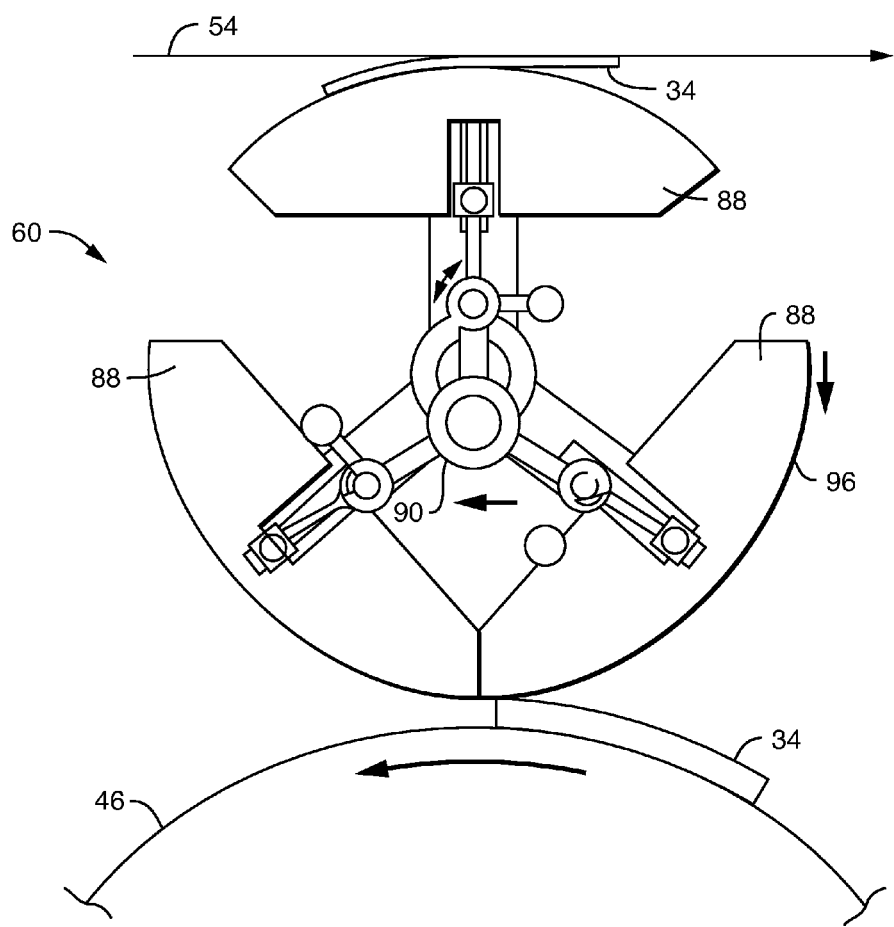
FIG. 7 is a front elevation view of an embodiment of an oscillating cam adjusted roll.

As noted above, an alternate applicator 56 may be an oscillating cam adjusted roll 60. Referring now to FIG. 7, there is representatively shown an aspect of the oscillating cam adjusted roll 60 receiving a discrete portion 34 from the anvil roll 46. The oscillating cam adjusted roll 60 may bond the discrete part 34 to a second web 54 traveling at a second speed. The illustrated example of the oscillating cam adjusted roll 60 has three transfer segments 88 which are configured to receive and bond the discrete part 34. It should be readily understood that the oscillating cam adjusted roll 60 may include any number of transfer segments 88 depending upon the different web speeds and desired placement and size of the discrete part 34. Each transfer segment 88 may be configured to be rotated by a drive ring 90 such that the surface speed of each transfer segment 88 may be substantially equal to the speed of the anvil roll 46 as the discrete part 34 is received and substantially equal to the speed of the second web 54 as the discrete part 34 is applied to the second web 54.

The outer surface 96 of each transfer segment 88 travels along and defines a common circumferential path that allows the discrete part 34 to be received and bonded to the second web 54. The outer surface 96 is configured to receive at least one discrete part 34 and apply the discrete part 34 to the second web 54 on each revolution. In an embodiment, the outer surface 96 of each transfer segment 88 may also be configured to rotate the discrete parts 34 before the discrete part 34 is applied to the second web 54. Any turning mechanism which provides the desired rotation of the discrete part 34 can be used. For example, one suitable mechanism is a barrel cam as are well known to those skilled in the art. Thus, in use, the discrete part 34 may be received by the transfer segment 88 while oriented in one direction and, subsequently, be rotated by the turning mechanism before being applied to the second web 54. The turning mechanism can be configured to rotate the discrete part 34 any amount before it is bonded to the second web 54. For example, the turning mechanism may be configured to rotate the discrete part 34 from about 1 or 5 to about 90 or 180 degrees before it is bonded to the second web 54 depending upon the desired orientation of the discrete part 34 on the second web 54.

In an embodiment, the outer surface 96 of each transfer segment 88 may be textured to define a surface roughness which assists in gripping and maintaining the discrete part 34 on the outer surface 96. To assist in maintaining the discrete part 34 on the outer surface 96 of each transfer segment 88, the outer surface 96 may also include a plurality of holes therein through which a vacuum can be drawn. The number and pattern of the holes through which the vacuum may be drawn may vary depending upon the size of the transfer segment 88, the shape and size of the discrete part 34 and the desired location of the discrete part 34 on the transfer segment 88.

If vacuum is desired, the vacuum may be drawn through the holes in the outer surface 96 by one or more sources of vacuum using conventional techniques for drawing a vacuum as are known to those skilled in the art. The vacuum to each transfer segment 88 may also be controlled such that a vacuum is only being drawn from the outer surface 96 of each transfer segment for the period of its rotation when the discrete part 34 is located on the outer surface 96. For example, the vacuum may be activated just prior to the discrete part 34 being received and inactivated immediately after the discrete part 34 is bonded to the second web 54.

Additional information regarding the oscillating cam adjusted roller can be found in U.S. Pat. No. 5,716,478 to Boothe, et al. which is herein incorporated by reference.

The second web 54 can be unrolled from a second supply roll 70 and can be any kind of material as desired. Typical materials include, but are not limited to, paper, cellulose fibers, pulp, plastic film, cloth, non-woven materials including spunbond, as well as various synthetic and non-synthetic materials. Other materials can also be used. The second web 54 can be a composite formed from two or more similar or different materials. The second web 54 can be a laminate formed from two or more layers of material. The second web 54 can be primed or treated with a coating. The second web 54 can be flexed or otherwise manipulated to provide certain desirable properties. Furthermore, the second web 54 can be a continuous thin sheet or strip or it can have a three dimensional profile. For example, the second web 54 can be flat, lofty or bulky and may vary in thickness in the longitudinal and/or transverse directions.

In an embodiment, the second web 54 may be a virgin web. A virgin web is a web that has no additional layers, attachments or modifications thereto. In an embodiment, the second web 54 may have been at least somewhat processed, for example, scored, slitted, or had other discrete portions applied thereon. For example, for a disposable absorbent article, several discrete portions of elastic or other material may have already been applied to the second web 54 before the discrete portion 34 is added.

The second web 54 can have any width that will be accommodated by the manufacturing equipment it is designed to run on. In an embodiment, the width of the second web 54 may be equal to or less than about 36, 30, 24, 20, 18, 15, 10, 7, 6, 5, 4, 3 or 2 inches. The length of the second web 54, measured parallel to the machine direction, is generally greater than the width of the second web 54. The length of the second web 54 should be as long as practicably feasible so as to decrease the number of changeovers required. The second web 54 is generally considered "continuous" if it has only one beginning and one ending point on the second supply roll 70.

In an embodiment, an adhesive 72 can be dispensed from a mechanism 74, such as a spray nozzle, a slot coater, a bead applicator, etc. onto at least one surface of the second web 54. In an embodiment, the adhesive 72 can be in the form of a liquid bath that is retained in a container 76. A roller 78 can be positioned relative to the container 76 so as to apply the adhesive 72 onto one surface of the discrete portion 34 while the discrete portion 34 is held by vacuum onto the outer surface of the applicator 56. It should be understood that the adhesive 72 could be applied by other means known to those skilled in the art.

The second web 54 may be advanced from the second supply roll 70 around one or more guide rolls 80 (only one of which is depicted). The number of guide rolls 80 will vary depending on a number of factors, such as the length and width of the second web 54, the distance the second web 54 has to travel, the desired tension, as well as other factors known to those skilled in the art.

The second web 54 may be advanced between a gap 82 formed between the applicator 56 and a backing roll 84. The backing roll 84 may be positioned in close proximity to the applicator 56 and may cooperate therewith. The backing roll 84 can have a diameter larger than, equal to or smaller than the diameter of the applicator 56. In an embodiment, the applicator 56 may have a larger diameter than the backing roll 84. The backing roll 84 can have a rotational speed equal to that of the second web 54. The second web 54 may be advanced by a feed mechanism 86 that is located downstream of the gap 82. The feed mechanism 86 can consist of various equipment including a pair of feed rolls, one or more process rolls, a vacuum conveyor, die rolls, functional rolls, S-wrapped rolls, nip rolls, etc. The purpose of the feed mechanism 86 is to pull or draw the second web 54 along at a steady speed. In an embodiment, the feed mechanism 86 is a process roll.

In FIG. 1, the backing roll 84 is rotating in a counter-clockwise direction and is arranged in close proximity to the applicator 56. It should be understood that the rotation of the equipment can be arranged as deemed suitable by one of ordinary skill. The gap 82 formed between these two rolls, 56 and 84, can be large enough to enable the discrete portion 34 and the second web 54 to pass therebetween without being unduly compressed. In an embodiment, the gap 82 can be dimensioned to provide a passage for the discrete portion 34 and the second web 54 with limited compression.

The backing roll 84 can be used to help bond the discrete portion 34 to the second web 54. The backing roll 84 can be a driven roll that can be rotated by a motor or a belt drive. If the material forming the second web 54 is stiff, the backing roll 84 does not have to be driven but could be freely rotatable. It should also be noted that for some methods, the backing roll 84 could be replaced by a stomper roll, a vacuum screen, a belt, a vacuum conveyor, a movable web or some other device capable of providing the necessary compression to produce the pressure necessary to bond the discrete portion 34 to the second web 54.

Once the discrete portion 34 has been brought into contact with the second web 54 and is either positioned thereon or is bonded thereto, a combination web 130 is formed. This combination web 130 can be a continuous strip or can be cut into individual segments. The combination web 130 can be wound on a roll, converted to a desired form, or transported to another process where it can be utilized to make a finished product. The combination of the discrete portion 34, adhesives 72 and other items applied to the second web 54 can produce a finished disposable absorbent article 200.

In an embodiment, when the discrete portion 34 and the second web 54 are combined, their surface speeds may be matched to be within at least about 5%, 3% or 1% of each other. By matching the speeds of the discrete portion 34 and the second web 54, shock loading can be reduced and wrinkles, gaps, and other defects can be eliminated. When the discrete portion 34 is combined with the second web 54 at different speeds, registration problems can occur. Furthermore, other downstream problems in the converting and/or in the packaging operations can occur when the speeds are not matched.

Once the discrete portion 34 is at least partially transferred from the applicator 56 onto the second web 54, the applicator 56 can be accelerated and decelerated back to a first speed that will match the speed of the anvil roll 46. This will enable the applicator 56 to accept another incoming discrete portion 34 from the anvil roll 46 while rotating at the same speed as the discrete portion 34. It should be understood that each step of the process described herein may occur while another step of the process described herein is also occurring. For example, forming and separating a discrete portion 34 from a first web 14 may occur while another discrete portion 34 is transferring from the converting mechanism 24 to the applicator 56 while yet another discrete portion 34 is transferring from the applicator 56 to a second web 54.

Figure 8:
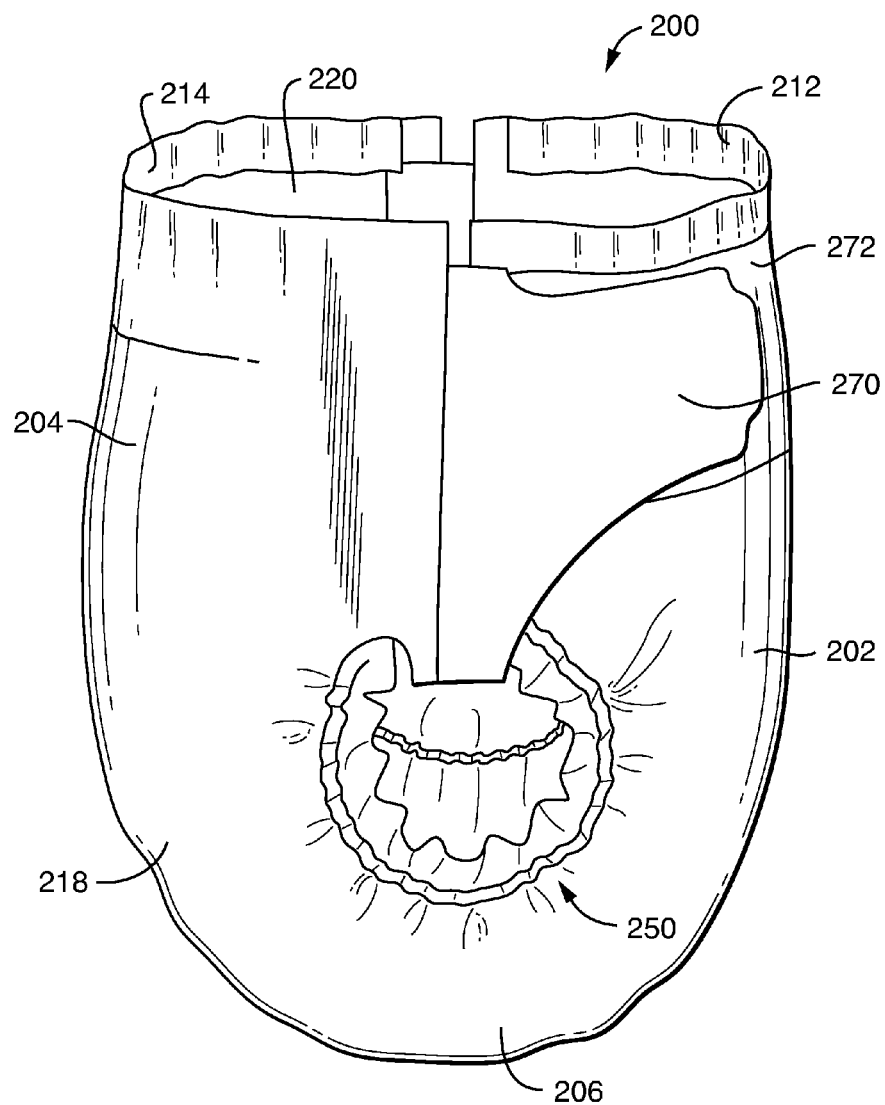
FIG. 8 is a side view illustration of an absorbent article.

Referring to FIG. 8, a disposable absorbent article 200 is exemplified in the form of a wearer's diaper. While the embodiments and illustrations described herein may generally apply to absorbent articles manufactured in the machine-direction, it should be noted that one of ordinary skill could apply the information herein to absorbent articles manufactured in the cross-direction without departing from the spirit and scope of the disclosure. The absorbent article 200 includes a front waist region 202, a back waist region 204, and a crotch region 206 interconnecting the front and back waist regions, 202 and 204, respectively. The absorbent article 200 has a pair of laterally opposite side edges, 208 and 210 (shown in FIG. 9), and a pair of longitudinally opposite waist edges, respectively designated front waist edge 212 and back waist edge 214. The front waist region 202 is contiguous with the front waist edge 212 and the back waist region 204 is contiguous with the back waist edge 212.

Figure 9:
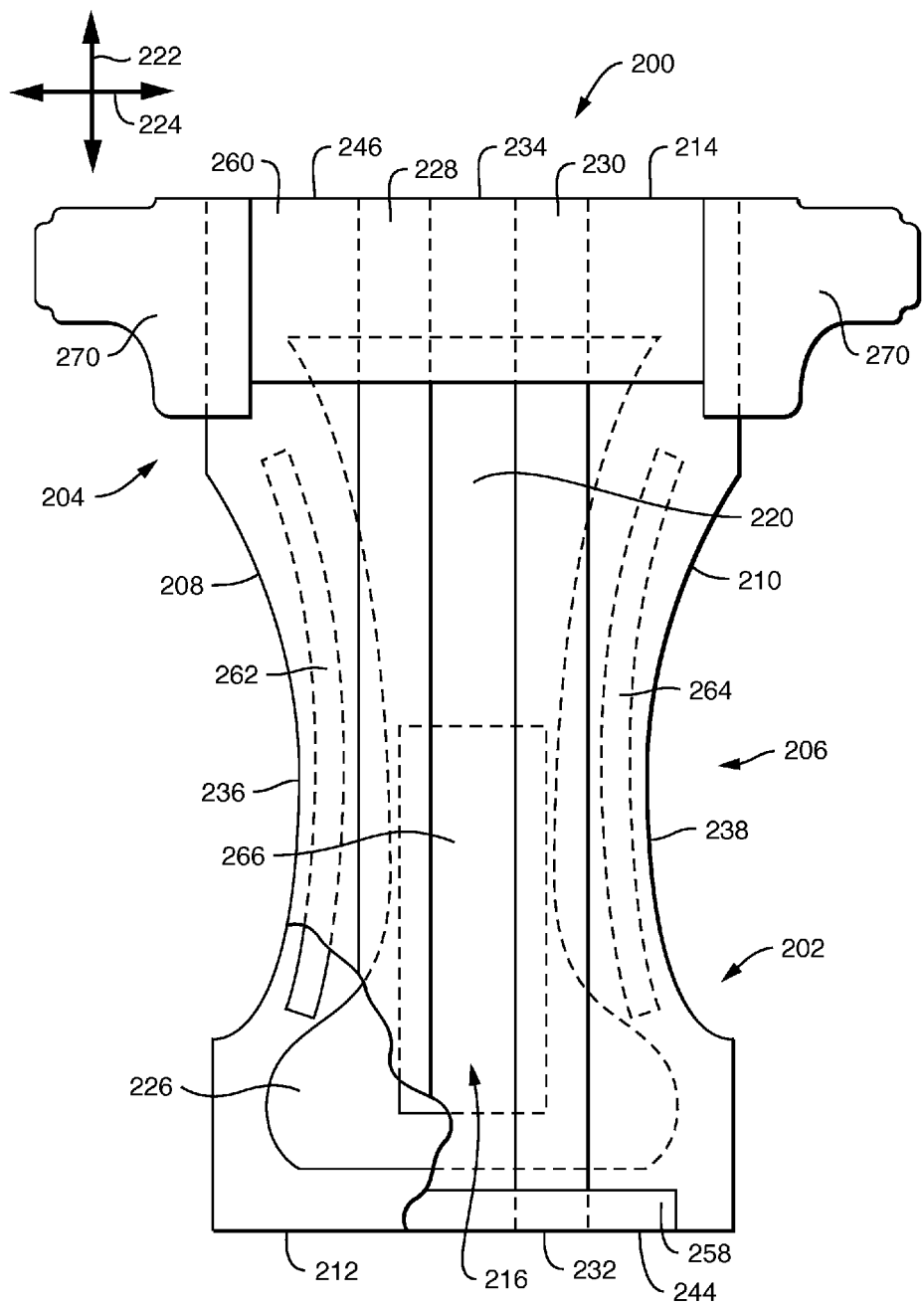
FIG. 9 is a top view illustration of the absorbent article of FIG. 8 in an unfolded, flat-out, uncontracted states (i.e., with all elastic induced gathering and contractions removed), with the bodyside liner facing the viewer and portions partially cut away to illustrate underlying features.

Referring to FIG. 9, the absorbent article 200 is illustrated in a stretched and laid flat configuration. The illustrated absorbent article 200 includes a central absorbent assembly 216 which can be rectangular or any other desired shape. The central absorbent assembly 216 includes an outer cover 218 and a bodyside liner 220 bonded to the outer cover 218 in a superposed relation by suitable means such as, but not limited to, adhesives, ultrasonic bonds, thermal bonds, or other conventional techniques. The outer cover 218 defines a length, or longitudinal direction 222, and a width, or lateral direction 224, which, in the illustrated embodiment, coincide with the length and width of the absorbent article 200. An absorbent core 226 is disposed between the outer cover 218 and the bodyside liner 220. A pair of containment flaps, 228 and 230, is secured to the bodyside liner 220 for inhibiting the lateral flow of body wastes. The central absorbent assembly 216 has opposite end edges, 232 and 234, that form portions of the front and back waist edges, 212 and 214, respectively, and opposite side edges, 236 and 238, that form portions of the side edges, 208 and 210, respectively, of the absorbent article 200. The absorbent core 226 comprises longitudinal side edges, 240 and 242, which may form portions of the side edges, 236 and 238, of the central absorbent assembly 216 and comprises end edges, 244 and 246, which may form portions of the opposite end edges, 232 and 234, of the central absorbent assembly 216. The absorbent core 226, therefore, may have a length and width that is the same as or less than the length and width of the central absorbent assembly 216.

The front waist region 202 includes the portion of the absorbent article 200 that, when worn, is positioned at least in part on the front of the wearer while the back waist region 204 includes the portion of the absorbent article 200 that, when worn, is positioned at least in part on the back of the wearer. The crotch region 206 of the absorbent article 200 includes the portion of the absorbent article 200 that, when worn, is positioned between the legs of the wearer and covers the lower torso of the wearer. The waist edges, 212 and 214, of the absorbent article 200 are configured to encircle the waist of the wearer and together define the central waist opening 248. Portions of the central absorbent assembly 216 side edges, 236 and 238, in the crotch region 206 generally define the leg openings 250.

The central absorbent assembly 216 is configured to contain and/or absorb liquid and solid wastes discharged from the wearer. For example, the containment flaps 228 and 230 are configured to provide a barrier to the lateral flow of body exudates. A flap elastic member can be operatively joined to each containment flap 228 and 230 in any suitable manner known in the art. The elasticized containment flaps 228 and 230 define a partially unattached edge that assumes an upright configuration in at least the crotch region 206 of the absorbent article 200 to form a seal against the wearer's body. The containment flaps 228 and 230 can be located along the central absorbent assembly 216 side edges 236 and 238 and can extend longitudinally along the entire length of the central absorbent assembly 216 or can extend partially along the length of the central absorbent assembly 216. Suitable construction and arrangements for containment flaps 228 and 230 are generally well known to those skilled in the art and are described in U.S. Pat. No. 4,704,116 issued Nov. 3, 1987 to Enloe, which is incorporated herein by reference.

To further enhance containment and/or absorption of body exudates, the absorbent article 200 suitably includes a front waist elastic member 258, a rear waist elastic member 260 and leg elastic members 262 and 264, as are known to those skilled in the art. The waist elastic members 258 and 260 can be attached to the outer cover 218 and/or the bodyside liner 220 along the opposite central absorbent assembly 216 end edges 232 and 234, and can extend over part or all of the central absorbent assembly 216 end edges 232 and 234. The leg elastic members 262 and 264 can be attached to the outer cover 218 and/or the bodyside liner 220 along the opposite central absorbent assembly 216 side edges 236 and 238 and positioned in the crotch region 206 of the absorbent article 200.

The outer cover 218 can be elastic, stretchable or non-stretchable and may be a multi-layer laminate structure of which at least one of the layers is liquid impermeable. In an embodiment, the outer cover 218 can be suitably stretchable and more suitably elastic in at least the lateral or circumferential direction of the absorbent article 200. In another embodiment, the outer cover 218 can be stretchable, and more suitably elastic, in both the lateral and the longitudinal directions. In an embodiment, the outer cover 218 may be a two layer construction, including an outer layer constructed of a liquid permeable material and an inner layer constructed of liquid impermeable material bonded together by a laminate adhesive. Suitable laminate adhesives can be applied continuously or intermittently as beads, a spray, parallel swirls, or the like. It is to be understood that the outer cover 218 may instead be constructed of a single layer of impermeable material without departing from the scope of this disclosure.

The liquid permeable outer layer of the outer cover 218 can be any suitable material and may be one that provides a generally cloth-like texture to the wearer. One example of such material is a 20 gsm spunbond polypropylene non-woven web. The outer layer may also be constructed of the same materials from which the bodyside liner 220 is constructed as described herein. It is to be understood that it is not necessary for the outer layer of the outer cover 218 to be liquid permeable.

The liquid impermeable inner layer of the outer cover 218 can be either vapor permeable (i.e., "breathable") or vapor impermeable. The inner layer may be manufactured from a thin plastic film, although other liquid impermeable materials may also be used. The liquid impermeable inner layer (or the liquid impermeable outer cover 218 where the outer cover 218 is of a single-layer construction) inhibits liquid body waste from leaking out of the absorbent article 200 and wetting articles, such as bed sheets and clothing, as well as the wearer and care giver.

Where the outer cover 218 is of a single layer construction, it can be embossed and/or matte finished to provide a more cloth-like appearance. The outer cover 218 can permit vapors to escape from the absorbent article 200 while preventing liquids from passing through. A suitable liquid impermeable, vapor permeable material is composed of a microporous polymer film or a non-woven material which has been coated or otherwise treated to impart a desired level of liquid impermeability.

The absorbent core 226 is suitably constructed to be generally compressible, pliable, non-irritating to the wearer's skin and capable of absorbing and retaining liquid body waste, such as urine. The absorbent core 226 can be manufactured in a wide variety of sizes and shapes (for example, rectangular, trapezoidal, T-shape, I-shape, hourglass shape, etc.) and from a wide variety of materials. The size and the absorbent capacity of the absorbent core 226 should be compatible with the size of the intended wearer and the liquid loading imparted by the intended use of the absorbent article 200. Additionally, the size and the absorbent capacity of the absorbent core 226 can be varied to accommodate wearers ranging from infants to adults.

The absorbent core 226 may have a length ranging from about 200 mm to about 520 mm. The absorbent core 226 may have a crotch width ranging from about 50 mm to about 130 mm. The width of the absorbent core 226 located within the front waist region 202 and/or the back waist region 204 of the absorbent article 200 may range from about 80 mm to about 130 mm.

The absorbent core 226 may be constructed of two layers of materials, or in the alternative, may be constructed of a single layer of materials. In an embodiment, the absorbent core 46 comprises a first layer suitably composed of hydrophilic fibers and a second layer suitably composed at least in part of a high absorbency material commonly known as superabsorbent material. In an embodiment, the first layer of the absorbent core 226 is suitably composed of cellulosic fluff, such as wood pulp fluff, and the second layer of the absorbent core 226 is suitably composed of superabsorbent hydrogel-forming particles, or a mixture of cellulosic fluff and superabsorbent hydrogel-forming particles. As a result, the first layer has a lower absorbent capacity per unit weight than the second layer. The first layer may alternatively be composed of a mixture of hydrophilic fibers and superabsorbent material, as long as the concentration of superabsorbent material present in the first layer is lower than the concentration of superabsorbent material present in the second layer so that the first layer has a lower absorbent capacity per unit weight than the second layer. It is also contemplated that the second layer may be composed solely of superabsorbent material without departing from the scope of this disclosure.

Various types of wettable, hydrophilic fibers can be used in the absorbent core 226. Examples of suitable fibers include cellulosic fibers, synthetic fibers composed of cellulose or cellulose derivatives, such as rayon fibers; inorganic fibers composed of an inherently wettable material, such as glass fibers; synthetic fibers made from inherently wettable thermoplastic polymers, such as particular polyester or polyamide fibers composed of nonwettable thermoplastic polymer, such as polypropylene fibers which have been hydrophilized by suitable means. The fibers may be hydrophilized, for example, by treatment with a surfactant, treatment with silica, treatment with a material which has a suitable hydrophilic moiety and is not readily removed from the fiber, or by sheathing the nonwettable, hydrophobic fiber with a hydrophilic polymer during or after formation of the fiber. For example, one suitable type of fiber is a wood pulp that is a bleached, highly absorbent sulfate wood pulp containing primarily soft wood fibers. However, the wood pulp can be exchanged with other hydrophilic fiber materials, such as synthetic, polymeric, or meltblown fibers or with a combination of meltblown and natural fibers.

Suitable superabsorbent materials can be selected from natural, synthetic, and modified natural polymers and materials. The superabsorbent materials can be inorganic materials, such as silica gels, or organic compounds, such as cross-linked polymers. Cross-linking may be covalent, ionic, Van der Waals, or hydrogen bonding. Examples of superabsorbent materials include polyacrylamides, polyvinyl alcohol, ethylene maleic anhydride copolymers, polyvinyl ethers, hydroxypropyl cellulose, carboxymal methyl cellulose, polyvinylmorpholinone, polymers and copolymers of vinyl sulfonic acid, polyacrylates, polyacrylamides, polyvinyl pyrrolidone, and the like. Additional polymers suitable for superabsorbent material include hydrolyzed, acrylonitrile grafted starch, acrylic acid grafted starch, polyacrylates and isobutylene maleic anhydride copolymers and mixtures thereof. The superabsorbent material may be in the form of discrete particles. The discrete particles can be of any desired shape, for example, spiral or semi-spiral, cubic, rod-like, polyhedral, etc. Shapes having a largest greatest dimension/smallest dimension ratio, such as needles, flakes, and fibers are also contemplated for use herein. Conglomerates of particles of superabsorbent materials may also be used in the absorbent core.

The absorbent core 226 overlays the inner layer of the outer cover 218, extending laterally between the leg elastic members, 262 and 264, and is secured to the inner layer of the outer cover 218, such as by being bonded thereto with adhesive. However, it is to be understood that the absorbent core 226 may be unsecured to the outer cover 218 and remain within the scope of this disclosure.

The absorbent core 226 may be partially or completely encompassed by a core wrap (not shown). The core wrap maintains the integrity and/or shape of the absorbent core 226. The core wrap may be well-suited for containing absorbent cores which are made at least partially of particulate material such as superabsorbent material. The core wrap can be composed of a cellulosic material, such as creped material or a high wet-strength tissue, a meltblown web, a spunbond web, a carded web, or a combination thereof. Once the core wrap has been wrapped around the absorbent core 226, the core wrap should not unduly expand or stretch as this might cause particulate material to escape from the absorbent core 226. In an embodiment, the core wrap, while in a dry state, should have respective elongation values at peak load in the machine and cross directions of 30 percent or less and 40 percent or less. In an embodiment, the core wrap may have a longitudinal length the same as the longitudinal length of the absorbent core 226.

In an embodiment, the core wrap completely wraps around the absorbent core 226 and is sealed to itself. In an embodiment, the core wrap may be folded over on itself and then sealed using, for example, heat and/or pressure. In an embodiment, the core wrap may be composed of separate sheets of core wrap which are utilized to encapsulate the absorbent core 226 and sealed together using a sealing means such as an ultrasonic bonder or other thermochemical bonding means or the use of an adhesive. Additional details regarding the core wrap may be found in U.S. Pat. No. 5,458,592 issued Oct. 17, 1995 to Abuto et al. which is herein incorporated by reference. It should be noted that it is not necessary that the absorbent core 226 is encompassed by a core wrap.

A surge layer, such as surge layer 266 may help decelerate and diffuse surges or gushes of liquid body waste penetrating the bodyside liner 220. The surge layer 266 may have any longitudinal length dimension as deemed suitable. In an embodiment, the longitudinal length of the surge layer 266 is the same as the longitudinal length of the absorbent core 226. In such an embodiment the midpoint of the longitudinal length of the surge layer 266 substantially aligns with the midpoint of the longitudinal length of the absorbent core 226. In an embodiment, the longitudinal length of the surge layer 266 is shorter than the longitudinal length of the absorbent core 226. In such an embodiment, the surge layer 266 may be positioned to be in liquid communication with the absorbent core 226 at any desired location along the longitudinal length of the absorbent core 226. As an example of such an embodiment, the absorbent core 226 may contain a target area where repeated liquid surges typically occur in the absorbent article 200. The particular location where liquid is discharged varies depending on the age and gender of the wearer. For example, males tend to urinate further toward the front end of the absorbent article 200 and the target area may be phased forward within the absorbent article 200. The female target area is located closer to the center of the crotch region 206 of the absorbent article 200. As a result, the relative longitudinal placement of the surge layer 266 within the absorbent article 200 can be selected to best correspond with the actual target area of either or both categories of wearers. In an embodiment, the absorbent core 226 may contain a target area centered within the crotch region 206 of the absorbent article 200 with the premise that the absorbent article 200 would be worn by a female wearer. The surge layer 266, therefore, may be positioned along the longitudinal length of the absorbent core 226 such that the surge layer 266 is substantially aligned with the target area of the absorbent article 200 intended for a female wearer. Alternatively, the absorbent article 200 may contain a target area positioned between the crotch region 206 and the front waist region 202 of the absorbent article 200 with the premise that the absorbent article 200 would be worn by a male wearer. The surge layer 266, therefore, may be positioned along the longitudinal length of the absorbent core 226 such that the surge layer is substantially aligned with the target area of the absorbent article 200 intended for a male wearer.

The surge layer 266 can rapidly accept and temporarily hold the liquid body waste prior to slowly releasing the liquid body waste for flow toward the absorbent core 266. The surge layer 266 can include various types of woven and non-woven fabrics, such as spunbond fabrics, meltblown fabrics, bonded carded webs, through-air bonded carded webs, knit fabrics, woven fabrics, airformed fabrics and the like, as well as combinations thereof. In an embodiment, the surge layer 266 may be an apertured film. The fabrics can be composed of various types of fibers, such as polyolefin fibers, polyester fibers, bicomponent fibers, conjugate fibers, curly fibers, and the like, as well as combinations thereof. The fibers may be short staple length fibers such as are used in the airlaying, bonding and carding processes, or longer more continuous fibers such as formed in the spunbond process. Typical staple length fiber lengths may range from about 5, 15, 20, 25, 30, 35 to about 40, 45, 50, or 55 millimeters, though lengths outside of this range may also be used. As a non-limiting example, airlaying typically involves using fibers with lengths in the range of about 5 to about 20 millimeters. Fiber diameters typically may range from about 1.5 to about 16 denier, and in another embodiment, from about 3 to about 6 denier. The fibers of the surge layer 266 may be crimped, circular or noncircular including, for example, bilobal, trilobal, and x-shaped cross-sections. The fibers may be solid or hollow. Additionally, the fibers may be made from a single fiber polymer or from multiple polymers such as are commonly found in biconstituent and bi- or multicomponent fibers. When using bicomponent fibers, fiber cross-sections may include, for example, sheath/core, side-by-side and islands-in-the-sea cross sections. The resultant fibrous surge layer may be a uniformly mixed homogeneous single layer blend of the selected type fiber or fibers.

Examples of suitable surge layers are described in U.S. Pat. Nos. 5,486,166; 5,490,846; 5,562,650; and 5,364,382, the entire disclosures of which are hereby incorporated by reference in a manner that is consistent herewith.

The bodyside liner 220 may be secured to the surge layer 266 such as by being bonded thereto using a suitable adhesive and to the absorbent core 226, such as by being bonded thereto by additional adhesive. However, it is understood that the bodyside liner 220 may be unsecured to the surge layer and/or to the absorbent core 226 without departing from the scope of this disclosure.

The bodyside liner 220 of the absorbent article 200 overlays the absorbent core 226 and the outer cover 218 and isolates the wearer's skin from liquid waste retained by the absorbent core 226. The bodyside liner 220 may be secured to the absorbent core 226, such as by being bonded thereto by an adhesive. The bodyside liner 220 extends beyond the absorbent core 226 to overlay a portion of the inner layer of the outer cover 218 and is secured thereto, such as by being bonded thereto by adhesive, to substantially enclose the absorbent core 226 between the outer cover 218 and the bodyside liner 220. The bodyside liner 220 may be slightly narrower than the outer cover 218, but it is also to be understood that the bodyside liner 220 and the outer cover 218 may be of the same dimensions, or the bodyside liner 220 may be sized larger than the outer cover 218, without departing from the scope of this disclosure. It is also contemplated that the bodyside liner 220 may not extend beyond the absorbent core 226 and may not be secured to the outer cover 218 and/or to the absorbent core 226. The bodyside liner 220 is suitably compliant, soft feeling, and non-irritating to the wearer's skin and can be less hydrophilic than the absorbent core 226 to provide a relatively dry surface to the wearer and permit liquid body waste to readily penetrate through its thickness. Alternatively, the bodyside liner 220 can be more hydrophilic or can have essentially the same affinity for moisture as the absorbent core 226 to present a relatively wet surface to the wearer to increase the sensation of being wet. This wet sensation can be useful as a training aid. The hydrophilic/hydrophobic properties can be varied across the length, width and/or depth of the bodyside liner 220 and absorbent core 226 to achieve the desired wetness sensation of leakage performance.

The bodyside liner 220 can be manufactured from a wide selection of web materials, such as synthetic fibers (for example, polyester or polypropylene fibers), natural fibers (for example, wood or cotton fibers), a combination of natural and synthetic fibers, porous foams, reticulated foams, apertured plastic films, or the like. Various woven and non-woven fabrics can be used for the bodyside liner 220. For example, the bodyside liner 220 can be composed of a meltblown or spunbond web of polyolefin fibers. Alternatively, the bodyside liner 220 can be a bonded-carded web composed of natural and/or synthetic fibers. The bodyside liner 220 can be composed of a substantially hydrophobic material, and the hydrophobic material can, optionally, be treated with a surfactant or otherwise processed to impart a desired level of wettability and hydrophilicity. The surfactant can be applied by any conventional means, such as spraying, printing, brush coating, or the like. The surfactant can be applied to the entire bodyside liner 220 or it can be selectively applied to particular sections of the bodyside liner 220.

A suitable bodyside liner 220 may be constructed of a non-woven bicomponent web. The non-woven bicomponent web can be a spunbonded bicomponent web, or a bonded-carded bicomponent web. An example of a bicomponent staple fiber includes a polyethylene/polypropylene bicomponent fiber. In this particular bicomponent fiber, the polypropylene forms the core and the polyethylene forms the sheath of the fiber. Fibers having other orientations, such as multi-lobe, side-by-side, end-to-end may be used without departing from the scope of this disclosure.

Although the outer cover 218 and bodyside liner 220 of the central absorbent assembly 216 can include elastomeric materials, it is contemplated that the central absorbent assembly 216 may instead be generally inelastic, wherein the outer cover 218, the bodyside liner 220 and the absorbent core 226 are composed of materials which are generally non-elastomeric. In an embodiment, the bodyside liner 220 can be stretchable, and more suitably elastic. In an embodiment, the bodyside liner 220 is suitably stretchable and more suitably elastic in at least the lateral or circumferential direction of the absorbent article 200. In other aspects, the bodyside liner 220 can be stretchable, and more suitably elastic, in both the lateral and the longitudinal directions.

Fasteners 270 may be employed to secure the absorbent article 200 on a wearer. The fasteners 270 may be situated in the rear waist region 204 of the absorbent article 200 and located along a longitudinally extending side edge, 208 and 210. The fasteners 270 may be configured to encircle the hips of the wearer and engage the outer cover 218 in the front waist region 202 of the absorbent article 200 for holding the absorbent article 200 on the wearer. Suitable fasteners 270 can include, but are not limited to, hook and loop fasteners, tape tab fasteners, mushroom fasteners, buttons, pins, snaps, cohesive fasteners, fabric-and-loop fasteners, or the like, may be employed. In an embodiment, the fasteners 270 may be releasably engageable with the outer cover 218 of the absorbent article 200. In an embodiment, the absorbent article 200 may include a fastening panel 272 (exemplified in FIG. 8) situation in the front waist region 202 of the outer cover 218. In such an embodiment, the fasteners 270 may be releasably engageable with the fastening panel 272 to maintain the absorbent article 200 about the waist of the wearer. In an embodiment, the fasteners 270 may include hook type fasteners and the front waist region 202 of the outer cover 218 may be configured to function as complimentary loops. In such an embodiment, the hook type fasteners may releasably engage with the outer cover 218 of the absorbent article. Such an arrangement can provide the ability to vary the size of the waist opening in small increments over a wide range to fit the waist of the wearer. The fasteners 270 may have a variety of shapes and sizes which provide the desired fastening of the absorbent article 200 about the waist of the wearer.

The absorbent article may have a pair of side panels to which the fasteners 270, such as the hook portion of a hook and loop fastener, are attached. Generally, the side panels 268 are bonded to the side edges of the absorbent article 200 in one of the waist sections, 202 or 204, and extend laterally outward therefrom. The side panels 268 may be elasticized or otherwise rendered elastomeric. In an embodiment, the side panels 268 may be an elastomeric material such as a neck-bonded laminate or a stretch-bonded laminate material. Methods of making such materials are described in U.S. Pat. No. 4,663,220 to Wisneski et al. which is herein incorporated by reference in its entirety. Examples of absorbent articles that include elasticized side panels and fastener tabs are described in U.S. Pat. No. 5,399,219 to Roessler et al., U.S. Pat. No. 5,540,796 to Fries, U.S. Pat. No. 5,595,618 to Fries each of which is hereby incorporated by reference in its entirety.

Containment flaps, 228 and 230, are secured to the bodyside liner 220 in generally parallel, spaced relation with each other laterally inward of the leg openings 250 to provide a barrier against the flow of urine to the leg openings 250. The containment flaps, 228 and 230, extend longitudinally from the front waist region 202 of the absorbent article 200, through the crotch region 206 to the back waist region 204 of the absorbent article 200. Each containment flap, 228 and 230, comprises a non-woven layer and a film layer secured to the non-woven layer, such as by being bonded thereto by adhesive. Flap elastics may be secured by suitable adhesive between the non-woven layer and the film layer, generally at a distal end of the containment flaps, 228 and 230, with the non-woven layer being folded over the flap elastics and the film layer at the distal end. The containment flaps, 228 and 230, are secured to the bodyside liner 220 by a seam of adhesive to define a proximal end of the containment flaps, 228 and 230.

The flap elastics may comprise strands of elastomeric material extending longitudinally along the distal ends of the containment flaps, 228 and 230, in generally parallel, spaced relation with each other. The elastic strands are secured between the non-woven layer and the film layer while in an elastically contractible condition such that contraction of the strands gathers and shortens the distal ends of the containment flaps, 228 and 230. As a result, the elastic strands bias the distal ends of each containment flap, 228 and 230, toward a position spaced from the proximal end of the containment flaps, 228 and 230, so that the containment flaps, 228 and 230, extend away from the bodyside liner 220 in a generally upright orientation of the containment flaps, 228 and 230, especially in the crotch region 206 of the absorbent article 200, when the absorbent article 200 is fitted on the wearer. It is understood, however, that the containment flaps, 228 and 230, may be omitted from the absorbent article 200 without departing from the scope of this disclosure.

Leg elastic members, 262 and 264, are secured between the outer and inner layers of the outer cover 218, such as by being bonded therebetween by a laminate adhesive, generally adjacent the lateral outer edges of the inner layer of the outer cover 218. Alternatively, the leg elastic members, 262 and 264, may be disposed between other layers of the absorbent article 200. A wide variety of elastic materials may be used for the leg elastic members, 262 and 264. Suitable elastic materials include sheets, strands or ribbons of natural rubber, synthetic rubber, or thermoplastic elastomeric materials. The elastic materials can be stretched and secured to a substrate, secured to a gathered substrate, or secured to a substrate and then elasticized or shrunk, for example with the application of heat, such that the elastic retractive forces are imparted to the substrate.

In an embodiment, the absorbent article may be a pant-like absorbent article, such as youth training pants. In such an embodiment, the absorbent article can have side panels (not shown). In an example, the side panels can be secured to the inner or outer side of the outer cover, such as being bonded thereto by adhesive, by pressure bonding, by thermal bonding or by ultrasonic bonding. Alternatively, the side panels may be formed integrally with the absorbent article, such as by being formed integrally with the outer cover, the bodyside liner or other layers of the absorbent article. Each of the side panels can be constructed of one or more individual, distinct pieces of material. For example, each side panel can include first and second side panel portions (not shown) joined at a seam (not shown), with at least one of the portions including an elastomeric material. In an embodiment, each distinct piece of material forming the side panel can be configured by the method described herein. In an embodiment, each distinct piece of material forming the side panel can have a design graphic and/or graphic as described herein. In such an embodiment, the design graphic and/or graphic can be configured on the material to show through other materials of the absorbent article, such as may occur if the side panel is bonded to the inner side of the outer cover. In an embodiment, the side panel may be bonded to the outer side of the outer cover and the design graphic and/or graphic may be readily visible. Alternatively, each individual side panel can be constructed of a single piece of material folded over upon itself along an intermediate fold line (not shown).

The side panels suitably include an elastic material capable of stretching laterally. Suitable elastic materials, as well as one described process for incorporating elastic side panels and into an absorbent article are described in the following U.S. Pat. No. 4,940,464 issued Jul. 10, 1990 to Van Gompel et al., U.S. Pat. No. 5,224,405 issued Jul. 6, 1993 to Pohjola, U.S. Pat. No. 5,104,116 issued Apr. 14, 1992 to Pohjola, and U.S. Pat. No. 5,046,272 issued Sep. 10, 1991 to Vogt et al.; all of which are incorporated herein by reference. As an example, suitable elastic materials include a stretch-thermal laminate (STL), a neck-bonded laminate (NBL), a reversibly necked laminate, or a stretch-bonded laminate (SBL) material. Methods of making such materials are well known to those skilled in the art and described in U.S. Pat. No. 4,663,220 issued May 5, 1987 to Wisneski et al., U.S. Pat. No. 5,226,992 issued Jul. 13, 1993 to Morman, and European Patent Application No. EP 0 217 032 published on Apr. 8, 1987 in the names of Taylor et al., and PCT application WO 01/88245 in the name of Welch et al., all of which are incorporated herein by reference. Other suitable materials are described in U.S. patent application Ser. No. 12/649,508 to Welch et al. and Ser. No. 12/023,447 to Lake et al., all of which are incorporated herein by reference. Alternatively, the side panels may include other woven or non-woven materials, such as those described above as being suitable for the outer cover or bodyside liner, mechanically pre-strained composites, or stretchable but inelastic materials.

A flow control layer (not shown) may be disposed between the first and second layers of the absorbent core 226 to retard the rate at which urine received into the absorbent core 226 passes from the first layer to the second layer. The flow control layer may have a width and length substantially the same as the widths and lengths of the first and second layers of the absorbent core 226. However, it is to be understood that the flow control layer may be narrower and/or shorter than the first and second layers or wider and/or longer than the first and second layers without departing from the scope of this disclosure. The flow control layer may be constructed of either an impermeable material or a permeable material, it being understood that the rate at which urine passes from the first layer of the absorbent core 226 to the second layer of the absorbent core 226 is generally a function of the permeability of the flow control layer. As an example, a suitable material from which the flow control layer may be constructed is a polypropylene or polyethylene film having apertures formed therein to permit urine to flow therethrough. The apertures may be sized in the range of about 1 mm to about 10 mm and the aperture density of the film may be less than or equal to about 14 apertures per square inch of the film. The thickness of the film may be less than or equal to about 0.003 inches. Another suitable material for construction of the flow control layer is a meltblown, hydrophobic non-woven material. The material suitably has a basis weight of about 0.6 ounces per square yard and a thickness of less than or equal to about 1 mm. It is also contemplated that the flow control layer may be constructed of other permeable materials without departing from the scope of this disclosure. As another example, a suitable impermeable material from which the flow control layer may be constructed is a film material, such as a polyethylene or polypropylene film, devoid of apertures to severely retard the flow of urine from the first layer of the absorbent core 226 to the second layer of the absorbent core 226. Urine received by the first layer of the absorbent core 226 is instead directed by the flow control layer to migrate outward (e.g., through the first layer of the absorbent core 226) toward peripheral edges of the flow control layer and then around the edges thereof to the second layer of the absorbent core 226.

Examples of absorbent article configurations are described in U.S. Pat. No. 4,798,603 to Meyer, et al., U.S. Pat. No. 5,176,668 to Bemardin, U.S. Pat. No. 5,176,672 to Bruemmer et al., U.S. Pat. No. 5,192,606 to Proxmire et al., and U.S. Pat. No. 5,509,915 to Hanson et al., each of which is hereby incorporated by references in its entirety.

In an embodiment, multiple absorbent articles can be manufactured having a discrete portion 34 formed from the first web 14. In an embodiment, an absorbent article can be manufactured having a discrete portion 34 formed from the first web 14 and a second absorbent article can be manufactured having a discrete portion 34 formed from the first web 14. In such an embodiment, the discrete portion 34 of the first absorbent article can be the same as or different from the discrete portion 34 of the second absorbent article. In an embodiment, a first absorbent article having a discrete portion 34 formed from the first web 14 and a second absorbent article having a discrete portion 34 formed from the first web 14 can be packaged together in a single package. In such an embodiment, the discrete portion 34 of the second absorbent article can be the same as or different than the discrete portion 34 of the first absorbent article. In an embodiment, the discrete portion 34 of the second absorbent article is different from the discrete portion 34 of the first absorbent article.

In an embodiment, multiple absorbent articles can be manufactured having a discrete portion 34 formed from the first web 14. In such an embodiment, a discrete portion 34 can be manufactured by the method as described herein and can be bonded to the second web 54 as described herein. In such an embodiment, the discrete portion 34 can be bonded to the second web 54 in a location where it can span across two absorbent articles prior to the two absorbent articles being severed into individual absorbent articles. For example, the discrete portion 34 can be bonded to the second web 54 in a location between the two absorbent articles that will form a waistband region of each of the individual absorbent articles. For example, the absorbent articles can be manufactured in a front-to-front configuration, a back-to-back configuration, or a front-to-back configuration and the discrete portion 34 can be bonded in an area where the two absorbent articles are still connected to each other. In such an embodiment, the discrete portion 34 can be cut at least one more time when the two connected absorbent articles are separated from each other to form two individual absorbent articles. It should be understood that the resulting cut edge when the two absorbent articles are separated can be a linear, non-linear, or partially linear cut edge.

In an embodiment, an absorbent article can be manufacturing having at least two discrete portions 34 formed from the same first web 14. Each discrete portion 34 can be a functional component, a visual aesthetic component, or combination thereof. Each discrete portion 34 can have a shape. In an embodiment, at least one of the discrete portions 34 can have a design graphic 26 associated therewith. In an embodiment, each discrete portion 34 can have a design graphic 26 associated therewith illustrating a graphic 28. The graphic 28 of each discrete portion 34 can be the same as or different from the graphic 28 of any other discrete portion 34 of the absorbent article. In an embodiment, the perimeter 30 of each design graphic 28 can illustrate a shape 32 which can the same as or different from a shape illustrated by the perimeter 30 of another design graphic 28 associated with another discrete portion 34. As described herein, the discrete portions 34 can take on multiple configurations.

In an embodiment, an absorbent article can have at least two discrete portions. In an embodiment, the discrete portions 34 can be formed from the same first web 14. In such an embodiment, a first discrete portion 34 can have a design graphic 26 associated therewith illustrating a first graphic 28 and the perimeter 30 of the design graphic 26 may illustrate a first shape 32. Further, in such an embodiment, a second discrete portion 34 can have a design graphic 26 associated therewith illustrating the first graphic 28 and the perimeter 30 of the design graphic 26 may illustrate the first shape 32.

In an embodiment, an absorbent article can have at least two discrete portions. In an embodiment, the discrete portions 34 can be formed from the same first web 14. In such an embodiment, a first discrete portion 34 can have a design graphic 26 associated therewith illustrating a first graphic 28 and the perimeter 30 of the design graphic may illustrate a first shape 32. Further, in such an embodiment, a second discrete portion 34 can have a design graphic 26 associated therewith illustrating the first graphic 28 and the perimeter 30 of the second design graphic 34 may illustrate a second shape 28.

In an embodiment, an absorbent article can have at least two discrete portions. In an embodiment, the discrete portions 34 can be formed from the same first web 14. In such an embodiment, a first discrete portion 34 can have a design graphic 26 associated therewith illustrating a first graphic 28 and the perimeter 30 of the design graphic 26 may illustrate a first shape 32. Further, in such an embodiment, a second discrete portion 34 can have a design graphic 26 associated therewith illustrating a second graphic 28 and the perimeter 30 of the second design graphic 34 may illustrate the first shape 32.

In an embodiment, an absorbent article can have at least two discrete portions. In such an embodiment, the discrete portions can be formed from the same first web 14. In such an embodiment, a first discrete portion 34 can have a design graphic 26 associated therewith illustrating a first graphic 28 and the perimeter 30 of the design graphic 26 may illustrate a first shape. Further, in such an embodiment, a second discrete portion 34 can have a design graphic 26 associated therewith illustrating a second graphic 28 and the perimeter 30 of the second design graphic 34 may illustrate a second shape 32.

Figure 10:
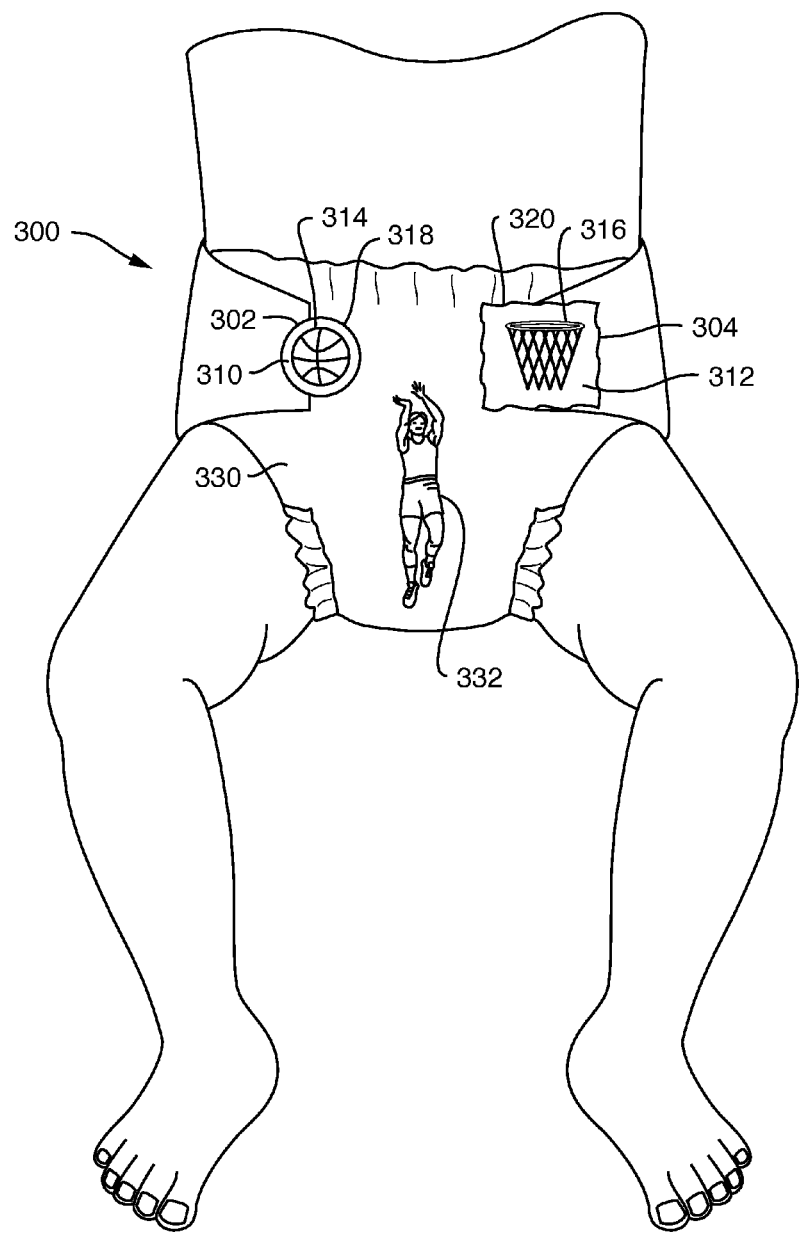
FIG. 10 is a front view of an embodiment of an absorbent article.

In an embodiment, an absorbent article can have at least two discrete portions. In such an embodiment, each discrete portion can have a complete and unitary design graphic associated therewith. Each design graphic of each discrete portion can be the same or can be different from each other. A complete and unitary design graphic is one that is a standalone graphic and does not need to interact with another component of the absorbent article or another design graphic in order to become complete. In an embodiment, the absorbent article can have an outer cover which can have a graphic associated therewith. In such an embodiment, the graphic associated with the outer cover of the absorbent article can be the same as or different from the design graphics of the discrete portions. In such an embodiment, the graphic of the outer cover can be a complete and unitary graphic. In such an embodiment, each of the design graphics can be visually related to each other such as, for example, by theme, color, activity, etc. As each of the design graphics can be visually related to each other, they can together form a picture when the absorbent article is assembled on the body of the wearer. It should be understood that the design graphics of the discrete portions and the graphic of the outer cover do not need to overlie each other in order to form the picture. FIG. 10 is an exemplary illustration of an embodiment of an absorbent article 300 having two discrete portions, 302 and 304. Each discrete portion, 302 and 304, has a design graphic, 310 and 312, associated therewith. As illustrated, each design graphic, 310 and 312, is a complete and unitary design graphic. Each design graphic, 310 and 312, illustrates a graphic, 314 and 316, and the perimeters, 318 and 320, of each design graphic, 310 and 312, each illustrate a shape of each discrete portion, 302 and 304. The first discrete portion 302 illustrates a graphic 314 of a basketball and the perimeter 318 of the first discrete portion 302 illustrates a circular shape. The second discrete portion 304 illustrates a graphic 316 of a basketball net and the perimeter 320 of the second discrete portion 304 illustrates a shape different from the round shape of the first discrete portion 302. The outer cover 330 of the absorbent article 300 illustrates a graphic 332 of a boy. When the absorbent article is assembled on the body of the wearer the three graphics, 314, 316 and 332, are visually related by a theme and together can form a picture, such as, for example, a boy playing basketball.

In the interests of brevity and conciseness, any ranges of values set forth in this disclosure contemplate all values within the range and are to be construed as support for claims reciting any sub-ranges having endpoints which are whole number values within the specified range in question. By way of hypothetical example, a disclosure of a range of from 1 to 5 shall be considered to support claims to any of the following ranges: 1 to 5; 1 to 4; 1 to 3; 1 to 2; 2 to 5; 2 to 4; 2 to 3; 3 to 5; 3 to 4; and 4 to 5.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

All documents cited in the Detailed Description are, in relevant part, incorporated herein by reference; the citation of any document is not to be construed as an admission that it is prior art with respect to the present invention. To the extent that any meaning or definition of a term in this written document conflicts with any meaning or definition of the term in a document incorporated by references, the meaning or definition assigned to the term in this written document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method of forming a first discrete portion and a second discrete portion from a first web, the method comprising the steps of:
   a. providing a first web;
   b. advancing the first web in a machine-direction to a converting mechanism, the converting mechanism comprising a rotary cutter comprising a first die cutter shape secured to the rotary cutter and a second die cutter shape secured to the rotary cutter, the first die cutter shape being different from the second die cutter shape;
   c. cutting the first web with the first die cutter shape secured to the rotary cutter to form the first discrete portion comprising a first shape without a linear cut edge in a cross-direction;
   d. separating the first discrete portion from the first web with the use of a vacuum, wherein the vacuum is pulled from within an anvil roll; and
   e. cutting the first web with the second die cutter shape secured to the rotary cutter to form the second discrete portion comprising a second shape that is different from the first shape of the first discrete portion; wherein cutting the first web with the first die cutter shape and the second die cutter shape provides the first web with the first shape followed by the second shape in an alternating sequence.

2. The method of claim 1 further comprising the step of removing the first web which is no longer attached to the first discrete portion.

3. The method of claim 1 further comprising the step of separating the second discrete portion from the first web.

4. The method of claim 1 wherein the first discrete portion is selected from the group consisting of a functional component of an absorbent article, a visual aesthetic component of an absorbent article, and combinations thereof.

5. The method of claim 4 wherein the first discrete portion comprises a design graphic.

6. The method of claim 1 wherein cutting the first web with the first die cutter shape secured to the rotary cutter to form the first discrete portion and separating the first discrete portion from the first web occur at the same time.

7. The method of claim 3 wherein cutting the first web with the second die cutter shape secured to the rotary cutter to form the second discrete portion and separating the second discrete portion from the first web occur at the same time.

8. The method of claim 1 wherein the alternating sequence provides the first web with the first discrete portion having the first shape followed by the second discrete portion having the second shape in a repeating sequence.

9. The method of claim 1 wherein the alternating sequence provides the first web with two discrete portions having the first shape followed by two discrete portions having the second shape in a repeating sequence.

10. The method of claim 1 wherein the first discrete portion is formed without having a connection to the second discrete portion.

11. A method of forming a first discrete portion and a second discrete portion from a first web, the method comprising the steps of:
   a. providing a first web;
   b. advancing the first web in a machine-direction to a converting mechanism, the converting mechanism comprising a rotary cutter comprising a first die cutter shape secured to the rotary cutter and a second die cutter shape secured to the rotary cutter, the first die cutter shape being different from the second die cutter shape;
   c. cutting the first web with the first die cutter shape secured to the rotary cutter to form the first discrete portion comprising a first shape without a linear cut edge in a cross-direction, wherein the first discrete portion is selected from the group consisting of a functional component of an absorbent article, a visual aesthetic component of an absorbent article, and combinations thereof;
   d. cutting the first web with the second die cutter shape secured to the rotary cutter to form the second discrete portion comprising a second shape that is different from the first shape of the first discrete portion; wherein cutting the first web with the first die cutter shape and the second die cutter shape provides the first web with the first shape followed by the second shape in an alternating sequence.

12. The method of claim 11 wherein the first discrete portion comprises a design graphic.

13. The method of claim 11 wherein the second discrete portion is selected from the group consisting of a functional component of an absorbent article, a visual aesthetic component of an absorbent article, and combinations thereof.

14. The method of claim 13 wherein the second discrete portion comprises a design graphic.

15. The method of claim 11, further comprising the steps of separating the first discrete portion from the first web; and separating the second discrete portion from the first web; wherein cutting the first web with the first die cutter shape secured to the rotary cutter to form the first discrete portion and separating the first discrete portion from the first web occur at the same time; and wherein cutting the first web with the second die cutter shape secured to the rotary cutter to form the second discrete portion and separating the second discrete portion from the first web occur at the same time.

16. The method of claim 11 wherein the alternating sequence provides the first web with the first discrete portion having the first shape followed by the second discrete portion having the second shape in a repeating sequence.

17. The method of claim 11 wherein the alternating sequence provides the first web with two discrete portions having the first shape followed by two discrete portions having the second shape in a repeating sequence.

18. The method of claim 11 wherein the first discrete portion is formed without having a connection to the second discrete portion.

\* \* \* \* \*